US008540948B2

(12) United States Patent
Loehn

(10) Patent No.: US 8,540,948 B2
(45) Date of Patent: Sep. 24, 2013

(54) LIDDED CONTAINER

(75) Inventor: Juergen Loehn, Gross Meckelsen (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 13/335,462

(22) Filed: Dec. 22, 2011

(65) Prior Publication Data

US 2012/0328490 A1 Dec. 27, 2012

(30) Foreign Application Priority Data

Dec. 23, 2010 (EP) .................. PCT/EP2010/007907

(51) Int. Cl.

| | |
|---|---|
| ***B01L 3/00*** | (2006.01) |
| ***B01L 99/00*** | (2010.01) |
| ***B67B 7/44*** | (2006.01) |
| ***G01N 21/75*** | (2006.01) |
| ***G01N 31/22*** | (2006.01) |
| ***G01N 33/52*** | (2006.01) |
| ***B04B 1/00*** | (2006.01) |
| *B65D 41/06* | (2006.01) |
| *B65D 41/36* | (2006.01) |
| *B65D 50/08* | (2006.01) |

(52) U.S. Cl.
USPC ........... 422/550; 220/293; 215/213; 215/253; 81/3.09; 422/400; 422/547; 422/548

(58) Field of Classification Search
USPC ................................................. 422/550, 568
See application file for complete search history.

(56) References Cited

U.S. PATENT DOCUMENTS 3,934,722 A 1/1976 Goldberg
5,253,551 A * 10/1993 DeVaughn .................... 81/3.09
5,270,011 A 12/1993 Altherr
5,674,456 A 10/1997 Chess et al.
5,863,791 A * 1/1999 Baldszun et al. .......... 435/288.1
6,398,067 B1 6/2002 Belfance et al.
2003/0102323 A1 6/2003 Lohn

FOREIGN PATENT DOCUMENTS

| | | | |
|---|---|---|---|
| DE | 3402278 | A1 | 8/1985 |
| EP | 0 487 448 | A1 | 5/1992 |
| EP | 0 841 093 | A2 | 5/1998 |
| EP | 0841093 | A2 | 5/1998 |
| EP | 1520624 | A1 | 4/2005 |
| EP | 1 731 443 | A1 | 12/2006 |
| WO | 95/13137 | A1 | 5/1995 |

* cited by examiner

*Primary Examiner* — Jill Warden
*Assistant Examiner* — Julie Tavares
(74) *Attorney, Agent, or Firm* — Vidas, Arrett & Steinkraus, P.A.

(57) ABSTRACT

A lidded container having a tubular container which at the bottom has a container base, at the top a container opening and below the container opening a sealing region on the internal wall, a lid which comprises a lid base and a plug protruding from the inside of the lid base, and which may be inserted through the container opening into a sealing position in the sealing region, and locking means for releasably locking the lid to the container comprising at least one latching projection projecting radially outward at the top edge of the container, at least one flexible and elastic connecting link projecting from the bottom side of the lid base on which a latching edge is arranged at a distance from the lid base vertically below the connection of the connecting link to the lid base.

22 Claims, 17 Drawing Sheets

17.2
16.2
15.2
15.1
16.1

2
6
14
14.2
6c
15.2
13
11
12.1
2.1
12.3
1.1
17
14.1
15.1
12.2
12

6
17.2
16.1
21
17
17.1
11
12
2
1.1

FIG.21
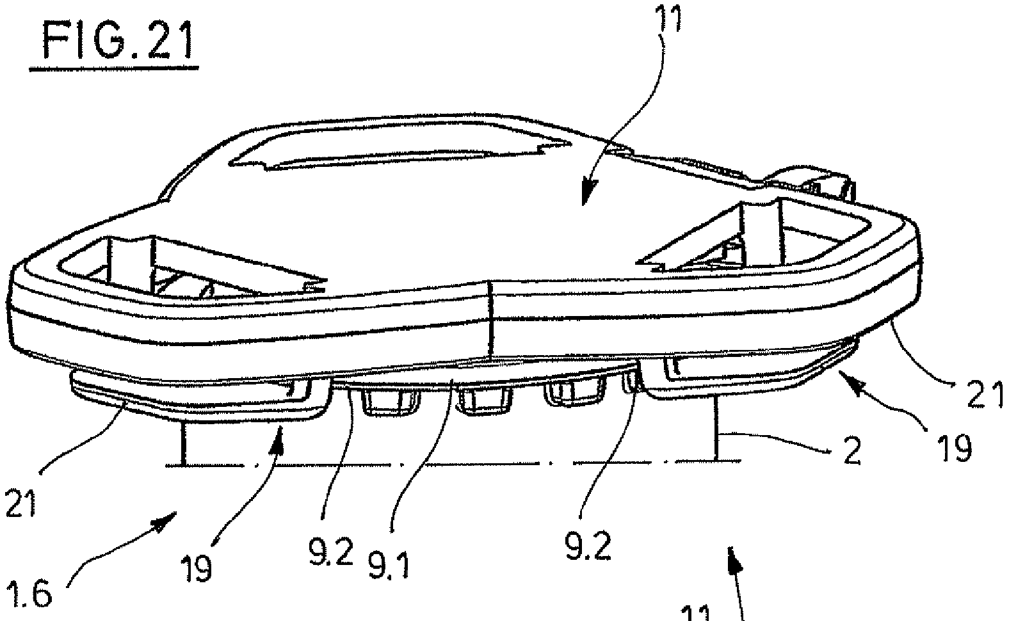
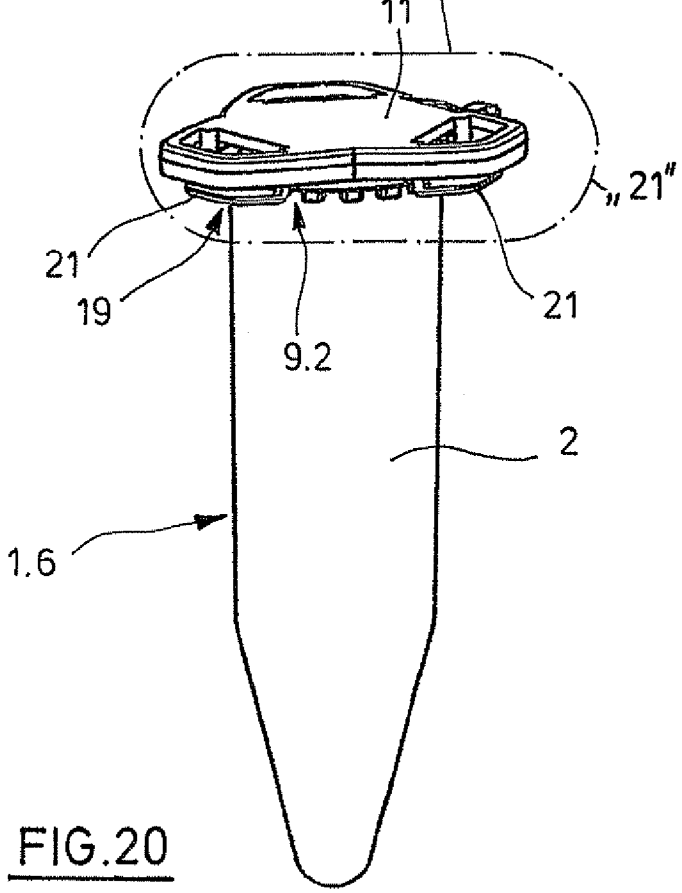
FIG.20

LIDDED CONTAINER

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a lidded container made of plastic for laboratory use.

Lidded containers of the aforementioned type typically have a capacity of a few tenths of a milliliter or several milliliters or one milliliter or less.

Known lidded containers made of plastics material for laboratory use comprise a tubular container which at the bottom has a container base, at the top a container opening and below the container opening a sealing region on the internal wall. A lid which comprises a lid base and a plug protruding from the inside of the lid base is able to be inserted through the container opening into a sealed position in the sealing region. The lid is sealed and held by the clamping force of the plug in the container. Applications exist in which a sample liquid filled into the container is heated and has an increased vapor pressure. For example, in polymerase chain reaction (PCR) technology, samples are repeatedly heated in the lidded containers, for example to temperatures of over 90° C. The level of the clamping force of the plug has to be such that sufficient vapor tightness is ensured and the lid is not released by the increased vapor pressure. As a result, it is necessary to apply a high degree of force in order to force the lid with the plug into the container. In order to open the lid the user has to press firmly against the lower edge of a protruding edge of the lid base.

BRIEF SUMMARY OF THE INVENTION

A lidded container of the aforementioned type is disclosed in EP 0 841 093 A2 and U.S. Pat. No. 5,863,791, in which the container and lid are integrally connected together in a pivotable manner via a strap hinge. The lid has a locking hook protruding downwards from a lid flange protruding to the side, and the container adjacent to the container opening has a locking cam behind which the locking hook is engaged in the closed position. When the lid is closed, the rigid locking hook snaps behind the locking cam through the resilient deformation of the lid flange, whereby the lid is secured in the closed position. To open the lid, the user has to force up the lid flange so that said lid flange is bent upwards and the locking hook is released from the locking cam. To this end, the locking hook and the locking cam only have a small overlap. Due to the small overlap, the locking hook may be inadvertently released from the locking cam, for example when the internal pressure rises in the container. When the lid is opened, the locking hook may be released abruptly from the locking cam, and as a result of which liquid samples may spray out of the container.

The lidded container has a support device which stabilizes the lid on the container opening in an intermediate position between an initial position pivoted away from the container opening by approximately 180° and a closed position.

In one embodiment of the lidded container, between the hinge straps two parallel fork arms extend from the container flange, between which a gap parallel to the hinge straps is formed. The fork arms have latching edges. A latching lug is oriented with the gap and is connected at its tip to the lid flange and at its base has latching projections on both sides. The latching lug is oriented with its latching projections perpendicular to the lid flange. If the lid is closed in the direction of the container opening, the latching lug enters the gap between the fork arms and forces said fork arms with their latching projections slightly apart. When the latching projections pass under the latching edges of the fork arms, said fork arms snap together slightly. If the lid is then released, the latching projections are held back by the latching edges and the lid is stabilized in the pivoted position which has been reached. It is a drawback here that during injection-molding the delicate fork arms form flow path ends which are difficult to ventilate due to their size. Air bubbles at the end of the flow path may lead to the formation of incomplete fork arms. The formation of complete fork arms is, however, necessary for the above-described pivoted position.

In a further embodiment, the support device comprises a latching lug which is formed as a hook protruding upwards from the plane of the container flange. The latching lug is arranged between flexible central portions of two parallel hinge straps, which are connected at one end to the container flange and at the other end to the lid flange. The lid flange has a latching edge between the hinge straps oriented perpendicular to the pivoting plane thereof A flexibility of the latching lug or respectively the hinge straps permits the latching edge to be raised over the end of the latching lug, when closing the lid. If the lid is then released, as a result of the resilience of the central portions it is pressed with the latching edge against the latching lug, so that it remains in this stable pivoted position in which the container is opened. To close the container, the lid is pivoted further and snapped with the locking hook behind the locking cam. It is a drawback here that the intermediate position may be difficult to reach due to the flexibility of the hinge straps. If, when pivoting the lid to the closed position, the user presses from above against the outer edge of the lid flange, the user displaces the lid downwards due to the flexibility of the hinge straps. As a result, the latching edge comes into contact with the latching lug at a low point and is only able to be pressed over the end of the latching lug by applying a high degree of force.

It is a drawback in both embodiments that the stability of the open position of the lid depends on the resilience of the strap portions. If the resilience is reduced, for example due to repeated closing and opening of the lid or by heating and/or cooling the container, the lid may move inadvertently out of the predetermined intermediate position and entirely or partially close the container opening. This may impair the filling and emptying of the lidded container.

In a further embodiment, two parallel hinge straps are also arranged between the container flange and the lid flange, the flexibility of said hinge straps being substantially concentrated on the narrowly defined region of a pivoting axis. The container flange and the lid flange are connected by a further hinge strap, which is arranged between the hinge straps. The further hinge strap has at one end a joint with the container flange and at the other end a joint with the lid flange. Between said two joints the hinge strap is of relatively thin configuration, so that it can be stretched in a resilient manner. After injection-molding the lidded container, the lid is bent back by approximately 180° from the container opening. In this initial position, the further hinge strap is not stretched. If the lid is now closed around the pivoting axis, the distance between the joints increases and the further hinge strap is slightly resiliently stretched until it is arranged on the pivoting axis, about which the lid may be pivoted relative to the container. If the lid is then pivoted further, the further hinge strap slightly contracts again, until it reaches its initial length. This is the case with an alignment of the lid of approximately 90° relative to the container opening. In this stable pivoted position, the lid is stabilized relative to the container by the further hinge strap. If the lid is closed further, the further hinge strap is bent outwards. When the lid is closed, the latching hook in cooperation with the latching cam prevents the lid from opening. After unlocking, the lid is again able to move back into its stable pivoted position or into the initial position.

It is a drawback with this lidded container that, due to the narrowly defined region of the pivot axis, the hinge straps do not permit any compensation movement when introducing the inventive sealing collar into the container opening. As a result, it is more difficult to close the lid. In the exemplary embodiments with flexible central portions of the hinge straps, however, the flexible central portions permit a compensation which simplifies the coaxial introduction of the sealing collar into the container.

EP 1 731 443 A1 describes a reaction vessel having a lid that can be opened using a lever mechanism. The lever must be pressed from above. Consequently, faulty operation can occur, for example when lidded containers are removed from a fully loaded centrifuge, or a fully loaded tube rack. Furthermore, the plug for the lid is kept short so that the container only has a slight vapor tightness. If the plug were lengthened, the lever would have to be lengthened to ensure easy opening, and this would further increase the risk of faulty operation.

U.S. Pat. No. 3,934,722 describes a package for sterile needles with a lid that can be opened using a lever mechanism. A lever is articulated to the edge of the container by means of a film hinge, and the inner lever arm of the lever can be placed on a container flange. The lid plug is levered out of the container by pressing on the bottom side of the outer lever arm. The lid is only secured in closed position by means of the clamping force of the plug in the container. The lever is only used to open the container.

U.S. Pat. No. 5,270,011 describes a reaction vessel with a lid that is only held in a closed position by means of a locking device consisting of a flexible connecting link and a locking pin. Bending the flexible connecting link and snapping it using the locking pin is difficult and generally requires the use of both hands. The same holds true for undoing the locking device.

U.S. Pat. No. 5,674,456 describes a substantially rectangular container for medical samples having a lid that can be closed or respectively opened using a snap lock. The lock is attached to the front of the lid. It has a vertical, two-arm lever that is centrally connected to the edge of the lid. The lower lever arm has a hook that engages below a projection on the edge of the container when the lid is in a locked state. The top lever arm is provided with a button that projects outward. When the button is pressed from below, the hook can be lifted out of latched position below the latching projection. The button is exposed so that faulty operation is quite possible.

U.S. Pat. No. 6,398,067 B1 describes a tamperproof lidded container, and on the top edge, the container has a releasable projection that possesses a hook and a break point. A lid has a joint and a connecting link with a first and second slot that are capable of receiving the projection. The second slot has a locking device. When the container is in an empty and sealed state, the projection is arranged in the first slot. When in a filled and sealed state, the projection is arranged in the second slot, and the hook engages with a locking device to form a tamperproof seal. To open the lid, the user must press against the connecting link with sufficient force from below so that the releasable projection tears off at its break point. The large amount of force required to release the seal and the releasable projection that become waste are disadvantageous.

WO 95/13137 A1 describes a lidded container having a closing lock that is actuated by rotating the lid in reference to the container. To open the lidded container, the lid must be turned in the opposite direction in reference to the container and then pulled out of the container with the plug. This requires two hands to use.

Known lidded containers with screwable lids seal tightly and reliably. However, the screw-on top makes it difficult or impossible to close and open the lidded container with only one hand.

Against this background, the invention is based on the object of creating a lidded container made of plastic for laboratory use that can be easily closed, reliably sealed and easily opened.

This object is achieved by a lidded container having the features of claim 1. Advantageous embodiments of the lidded container are cited in the dependent claims.

The lidded container according to the invention made of plastics material for laboratory use comprises

- a tubular container which at the bottom has a container base, at the top a container opening and below the container opening a sealing region on the internal wall,
- a lid which comprises a lid base and a plug protruding from the inside of the lid base, and which may be inserted through the container opening into a sealed position in the sealing region, and
- locking means for releasably locking the lid to the container having
- at least one latching projection projecting radially outward at the top edge of the container, and
- at least one flexible and elastic connecting link projecting from the bottom side of the lid base on which a latching edge is arranged at a distance from the lid base vertically below the connection of the connecting link to the lid base, and the latching connecting link can be snapped into the sealing area below the latching projection of the container when the plug is introduced.

The lidded container according to the invention can be sealed in a conventional manner by introducing the lid with the plug into the container opening and moving the lid into a sealing position in the sealing region. The user can thereby press against the rigid lid base. When the lid is being closed, the latching edge or a neighboring contour of the flexible connecting link slides over the latching projection, and the flexible connecting link is thereby deflected outward somewhat to the side. The latching edge then reaches the bottom margin of the latching projection, and is pivoted by the elastic connecting link below the bottom side of the latching projection. The lid is thereby locked to the container so that it is secured against being unintentionally opened. Given the flexibility of the connecting link, not much more force is required to close the lidded container than to close conventional lidded containers that do not have a latch. To this end, the connecting link can be designed particularly flexibly so that it can be easily deflected when closing the lid. Sufficient elasticity of the connecting link ensures that the latching edge automatically swings below the latching projection when the latching edge reaches the bottom margin of the latching projection. The latching edge is arranged vertically below the connection of the connecting link to the lid base so that the connecting link is only strained in the direction of pull by a vertical force exerted on the lid base, and the latching edge does not slip off of the latching projection. It is easy for the user to open the lidded container by pivoting the flexible connecting link outward. When the flexible connecting link is pivoted outward, the latching edge is released from the latching projection. By pressing upward, the unlocked lid is moved out of the container with the plug, and the container is opened.

Closing and opening can be performed with only one hand. A large overlap or respectively clamping force between the sealing plug and container is not required to sufficiently secure against independent opening. The associated greater force of closing and opening is avoided. The plug can be seated in the sealing position with comparatively low clamping force. The level of this clamping force can be set to ensure a sufficient vapor seal. Since there is a low clamping force, the lid can be easily lifted after the latch is released without the lid suddenly flying upward and spilling liquid or respectively releasing aerosols. It is particularly advantageous that the user can close the lidded container in a conventional manner by pressing down on the lid base, and then open the lidded container in a nearly conventional manner by pressing the connecting link outward and from below against the lid.

The object is also achieved by a lidded container having the features of Claim 2. Advantageous embodiments of the lidded container are cited in the dependent claims.

The lidded container according to the invention made of plastics material for laboratory use comprises

- a tubular container which at the bottom has a container base, at the top a container opening and below the container opening a sealing region on the internal wall,
- a lid which comprises a lid base and a plug protruding from the inside of the lid base, and which may be inserted through the container opening into a sealed position in the sealing region, and
- locking means for releasably locking the lid to the container having
- at least one latching projection projecting radially outward at the top edge of the container,
- at least one flexible and elastic connecting link projecting from the bottom side of the lid base on which a latching edge is arranged at a distance from the lid base that can be snapped into the sealing region below the latching projection when the plug is introduced, and
- a button projecting outward to the side from the connecting link, and the latching of the latching edge to the latching projection can be released by pressing against button from below.

The lidded container according to the invention can be sealed in a conventional manner by introducing the lid with the plug into the container opening and moving the lid into a sealing position in the sealing region. The user can thereby press against the rigid lid base. When the lid is being closed, the latching edge or a neighboring contour of the flexible connecting link slides over the latching projection, and the flexible connecting link is thereby deflected outward somewhat to the side. The latching edge then reaches the bottom margin of the latching projection, and is pivoted by the elastic connecting link below the bottom side of the latching projection. The lid is thereby locked to the container so that it is secured against being unintentionally opened. Given the flexibility of the connecting link, not much more force is required to close the lidded container than to close conventional lidded containers that do not have a latch. It is easy for the user to open the lidded container by pressing against the bottom side of the button. The flexible connecting link is thereby pivoted outward, and the latching edge releases from the latching projection. Because the button projects laterally from the connecting link, the outward pivoting motion of the connecting link is specifically controlled when the button is pushed. This can prevent the latching edge from suddenly releasing from the latching projection and liquid sample from splashing out of the container. By continuing to press upward, the unlocked lid is moved out of the container with the plug, and the container is opened.

Closing and opening can be performed with only one hand. A large overlap or respectively clamping force between the sealing plug and container is not required to sufficiently secure against independent opening. The associated greater force of closing and opening is avoided. The plug can be seated in the sealing position with comparatively low clamping force. The level of this clamping force can be set to ensure a sufficient vapor seal. Since there is a low clamping force, the lid can be easily lifted after the latch is released without the lid suddenly flying upward and spilling liquid or respectively releasing aerosols. It is particularly advantageous that the user can close the lidded container in a conventional manner by pressing down on the lid base, and then open the lidded container in a nearly conventional manner by pressing against the lid from below. He does not thereby press directly against the bottom side of the lid base but rather against the button located underneath which causes the latching to be released and the lid to lift. Incorrect use is prevented by arranging the button below the lid base.

According to an advantageous embodiment, the lidded container from claim 2 has the features of the lidded container of claim 1.

The object is also achieved by a lidded container having the features of Claim 4. Advantageous embodiments of the lidded container are cited in the dependent claims.

The lidded container according to the invention made of plastics material for laboratory use comprises

- a tubular container which at the bottom has a container base, at the top a container opening and below the container opening a sealing region on the internal wall,
- a lid which comprises a lid base and a plug protruding from the inside of the lid base, and which may be inserted through the container opening into a sealed position in the sealing region, and
- locking means for releasably locking the lid to the container having
- at least one latching projection projecting radially outward on the top edge of the container having a chamfer on the bottom side angled upward toward the container,
- at least one flexible and elastic connecting link projecting from the bottom side of the lid base on which a contact area with a latching edge is arranged on the side facing the container at a distance from the lid base and can snap under the latching projection when the plug is introduced into the sealing region so that the contact area is located below the lowest area of the latching projection with a section arranged further to the outside than the connection of the connecting link to the lid base, and the contact area lies against the chamfer when force is exerted vertically on the bottom side of the lid base.

The lidded container according to the invention can be closed in a conventional manner by introducing the lid with the plug into the container opening and moving the lid into a sealing position in the sealing region. The user can thereby press against the rigid lid base. When the lid is being closed, the latching edge or a neighboring contour of the flexible connecting link slides over the latching projection, and the flexible connecting link is thereby deflected outward somewhat to the side. The latching edge then reaches the bottom margin of the latching projection, and is pivoted by the elastic connecting link below the bottom side of the latching projection. The contact area with a section that is located further to the outside than the connection of the connecting link to the lid base thereby extends below the lowest region of the latching projection. The section can be an individual point, a line, a narrow strip, or a partial surface of the contact area. The lid is thereby locked to the container so that it is secured against being unintentionally opened. Given the flexibility of the connecting link, not much more force is required to close the lidded container than to close conventional lidded containers that do not have a latch. When the lid is lifted by an increase in the internal pressure of the container or a force exerted vertically on the lid base is increased, the lowest area of the latching projection presses against the section of the contact area, and the contact area lies against the chamfer on the bottom side of the latching projection. The contact area preferably lays flat against the chamfer. The contact area can however come to lay against the chamfer only at a minimum of a single point or area, for example with the latching edge. This is because the section is located further to the outside than the connection of the connecting link to the lid, and due to the flexibility of the connecting link and possibly the contact area. For an area of the contact area to lay against the chamfer, it is sufficient for the section to be arranged further to the outside than the middle of the connection of the connecting link to the lid base. The lid is thereby independently secured in the vessel. It is easy for the user to open the lidded container by pressing the flexible connecting link outward away from the container. When swinging the flexible connecting link outward, the latching edge is released from the latching projection. The user may press beforehand against the top side of the lid to release the contact area from the chamfer. By pressing upward, the unlocked lid is moved out of the container with the plug, and the container is opened.

Closing and opening can be performed with only one hand. A large overlap or respectively clamping force between the sealing plug and container is not required to sufficiently secure against independent opening. The associated greater force of closing and opening is avoided. The plug can be seated in the sealing position with comparatively low clamping force. The level of this clamping force can be set to ensure a sufficient vapor seal. Since there is a low clamping force, the lid can be easily lifted after the latch is released without the lid suddenly flying upward and spilling liquid or respectively releasing aerosols. It is particularly advantageous that the user can close the lidded container in a conventional manner by pressing down on the lid base, and then open the lidded container in a nearly conventional manner by pressing the connecting link outward and from below against the lid.

According to advantageous embodiments, the lidded container of Claim 4 comprises the features of the lidded container of at least one of Claims 1 to 3.

The object is also achieved by a lidded container having the features of Claim 6. Advantageous embodiments of the lidded container are cited in the dependent claims.

The lidded container according to the invention made of plastics material for laboratory use comprises

- a tubular container which at the bottom has a container base, at the top a container opening and below the container opening a sealing region on the internal wall,
- a lid which comprises a lid base and a plug protruding from the inside of the lid base, and which may be inserted through the container opening into a sealing position in the sealing region,
- locking means for releasably locking the lid to the container having
- at least one latching projection projecting radially outward at the top edge of the container, and
- a plurality of spaced flexible and elastic connecting links projecting from the bottom side of the lid base on which a latching edge is arranged at a distance from the lid base that can be snapped into the sealing region below the latching projection when the plug is introduced.

The lidded container according to the invention can be closed in a conventional manner by introducing the lid with the plug into the container opening and moving the lid into a sealing position in the sealing region. The user can thereby press against the rigid lid base. When the lid is being closed, the latching edge or neighboring contours of the flexible connecting links slide over at least one latching projection, and the flexible connecting links are thereby deflected outward somewhat to the side. The latching edges then reach the bottom margin of the latching projection, and is swung by the elastic connecting links below the bottom side of the latching projection. The lid is thereby locked to the container so that it is secured against being unintentionally opened. Given the flexibility of the connecting links, not much more force is required to close the lidded container than to close conventional lidded containers that do not have a latch.

Given the multiple latching of the lid to the container, the retention force can be multiplied. It is particularly advantageous that an even seal of the lid in the container can be achieved. For example, a lid with only one single latching to the container can be lifted a distance from the latch due to the increased internal pressure in the container in relation to the ambient pressure. This can occur in particular if the lid is connected to the container by means of a hinge in the form of a flexible strap hinge in addition to the latch since the strap hinge is yielding. According to the invention, lidded containers can in particular be designed with a hinge having a plurality of latches.

This effect increases with the size of the lid area. A plurality of latches can be advantageous, especially in the case of containers having a large capacity (such as 10 or more mL).

In addition, the invention relates to lidded containers where there is no hinge between the lid and container, and where the lid is connected to the container by means of a plurality of latches. The plurality of latches is preferably distributed evenly around the perimeter of the lidded container to evenly seal the lid in the container.

It is easy for the user to open the lidded container by pressing the flexible connecting links outward away from the container. When the flexible connecting links are swung outward, the latching edges are released from the latching projection. By pressing upward, the unlocked lid is moved out of the container with the plug, and the container is opened.

Closing and opening can be performed with only one hand. A large overlap or respectively clamping force between the sealing plug and vessel is not required to sufficiently secure against independent opening. The associated greater force of closing and opening is avoided. The plug can be seated in the sealing position with comparatively low clamping force. The level of this clamping force can be set to ensure a sufficient vapor seal. Since there is a low clamping force, the lid can be easily lifted after the latches are released without the lid suddenly flying upward and spilling liquid or respectively releasing aerosols.

According to advantageous embodiments, the lidded container of Claim 6 has the features of the lidded container of at least one of Claims 1 to 5.

The following embodiments generally apply to all inventions described above.

According to one embodiment, the latching projection is a flange that at least partially surrounds the perimeter of the top edge of the container. The top edge of the container is stabilized by the flange. The flange preferably runs completely around the top the edge of the container.

According to another embodiment, the latching projection on the outside and/or the connecting link on the inside has an outer and/or inner chamfer neighboring the latching edge so that the connecting link is increasingly deflected to the side when the plug is inserted into the container. As a result, the closing of the container is simplified.

According to one embodiment, the latching projection at the top and/or the connecting link at the bottom has a radius. This makes it easier to initially deflect the connecting link when it is being placed on the latching projection.

According to another embodiment, the lid base has a lid projection projecting laterally to the outside that extends radially beyond the latching projection when the plug is inserted into the sealing region to seal. The lid projection protects the connecting link or respectively button from being unintentionally actuated when the container is lifted by gripping the lid. The lid projection preferably extends outward radially at least as far as the button when the plug is inserted into the sealing region to seal.

According to one embodiment, the lid is connected to the container by means of a hinge. In this embodiment, the lid is undetachably connected to the container. The lid container can be closed and opened by simply pivoting the lid in relation to the container. The plug does not have to be specially aligned with the container opening.

According to another embodiment, the hinge is a strap hinge by means of which the container is integrally connected to the lid. The strap hinge may comprise one or more hinge straps which are at least partially flexible. The strap hinge is similar to a film hinge but may be flexible over a longer area perpendicular to the pivot direction. A strap hinge with at least one hinge strap which is flexible in at least one region in the longitudinal direction simplifies the insertion of the plug in the container opening of a cylindrical container as it permits a compensation movement. The monobloc connection of the container to the lid via the strap hinge enables the lidded container to be injection molded in a single injection molding step. The lidded container can also be injection molded as a single part in a plurality of injection molding steps from one or more plastics. The lid base is preferably connected via the strap hinge to the top edge of the container.

According to one embodiment, the latching edge is the bottom margin of a cutout in the connecting link. This design makes it easier to have a particularly large button that is located completely under the lid projection. This makes it easier to use the lidded container. This also favors the lid dimensions that are small enough for a plurality of lidded containers to be placed next to each other in a centrifuge rotor, tube rack or other device without hindering each other. Alternately, the latching edge can be formed on a latching projection of the connecting link that projects from the inside of the connecting link toward the container.

According to another embodiment, the connecting link has two lateral connecting link strips that are connected at the top to the lid base and at the bottom to the button, and the cutout is located between them. The two connecting link strips ensure the high flexibility of the connecting link. The button neighbors the cutout at the bottom so that the bottom edge of the cutout is the same as the inner, top edge of the button.

According to another embodiment, the connecting link has an individual connecting link strip that is connected at the top to the lid base and at the bottom to the button which is wider than the connecting link strip, and at least one inner, top margin of the button projecting laterally from the connecting link strip forms the latching edge. In this embodiment, the button is locked by means of at least one inner, top margin projecting laterally from the individual connecting link strip below the latching projection of the container.

According to another embodiment, the button is arranged in the direction of insertion of the plug below a congruent lid cutout in the lid projection. This embodiment allows the lid demolding by moving apart the parts of an injection mold in an axial direction.

According to another embodiment, the lid projection has a width that decreases toward the outside end of the lid projection. This favors a space-saving arrangement of several containers next to each other in a centrifuge, tube rack or other device.

According to another embodiment, a device for locking the lid in an opened position is next to the hinge. The device for locking can be designed as described in EP 0 841 093 A2 and U.S. Pat. No. 5,863,791 which is hereby included by means of reference. In addition, it can be designed as described in the following exemplary embodiments.

According to a further embodiment, the container, adjacent to the container opening, has an insertion region widening towards the upper edge of the container for the plug and the sealing region thereunder. As a result, the closing of the lidded container is simplified.

According to a further embodiment, the plug is a hollow cylinder. As a result, the plug is particularly flexible, whereby the closing and opening of the lidded container is further simplified.

According to a further embodiment, the plug has a peripheral sealing bead on the external periphery. As a result, the vapor tightness of the lidded container is further improved.

According to a preferred embodiment, the lidded container is produced by injection-molding. In the case of a lidded container without hinge, the lid and the container can be injection-molded separately.

The lidded container according to the invention is produced from one or more plastics materials. According to a further embodiment, the entire lidded container is produced from one or more elastic plastics. When the lidded container is produced from one or more elastic plastics, at least one connecting link is preferably more elastic than the lid and/or container. The connecting link can thereby be given a suitable shape, especially when the connecting link wall is thinner than the lid and/or the container. In addition, this can be achieved by selecting a particularly elastic plastic for the connecting link. The connecting link is preferably elastic enough so that primarily or exclusively the connecting link is elastically deformed when closing and opening the lid.

According to a further embodiment, the lidded container is produced from one or more polyolefins. Preferably, the lidded container consists of a polypropylene and/or a polyethylene. It is also possible to produce the lidded container with a plug made of different plastics materials which comprise harder and more flexible segments, as disclosed in US 2003/0102323 A1, which is incorporated in the invention by way of reference. The lidded container may be produced, in particular, in a multi-component injection-molding process.

BRIEF DESCRIPTION OF THE SEVERAL VIEWS OF THE DRAWINGS

The invention is explained in more detail hereinafter with reference to the accompanying drawings of exemplary embodiments. In the drawings:

FIG. 20 shows a lidded container having a plurality of latches with buttons and hinge between the lid and container in a perspective view at an angle from above and from the side;

FIG. 21 shows said lidded container in an enlarged partial perspective view from the same side;

DETAILED DESCRIPTION OF THE INVENTION

Figure 1:
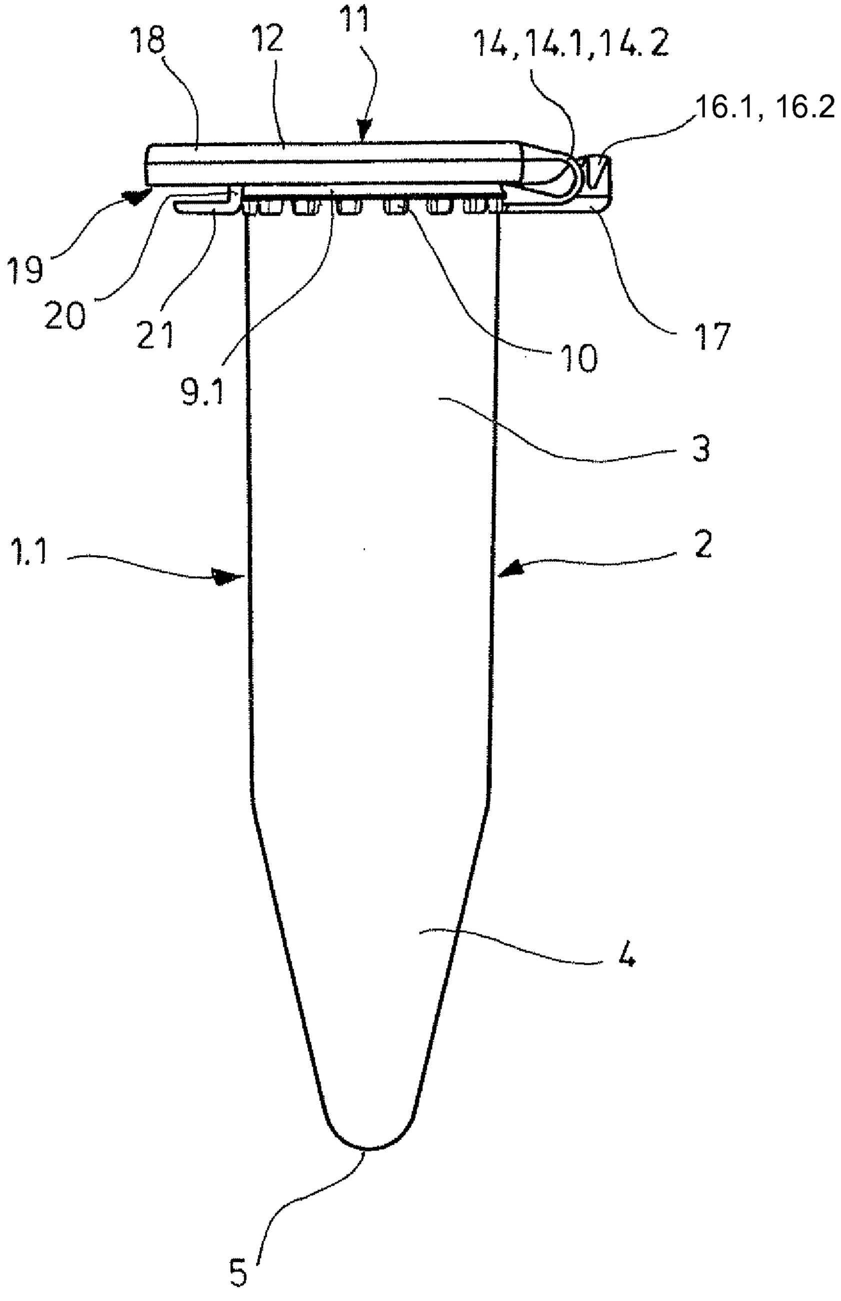
FIG. 1 shows a lidded container according to the invention in the closed state in a side view.
Figure 2:
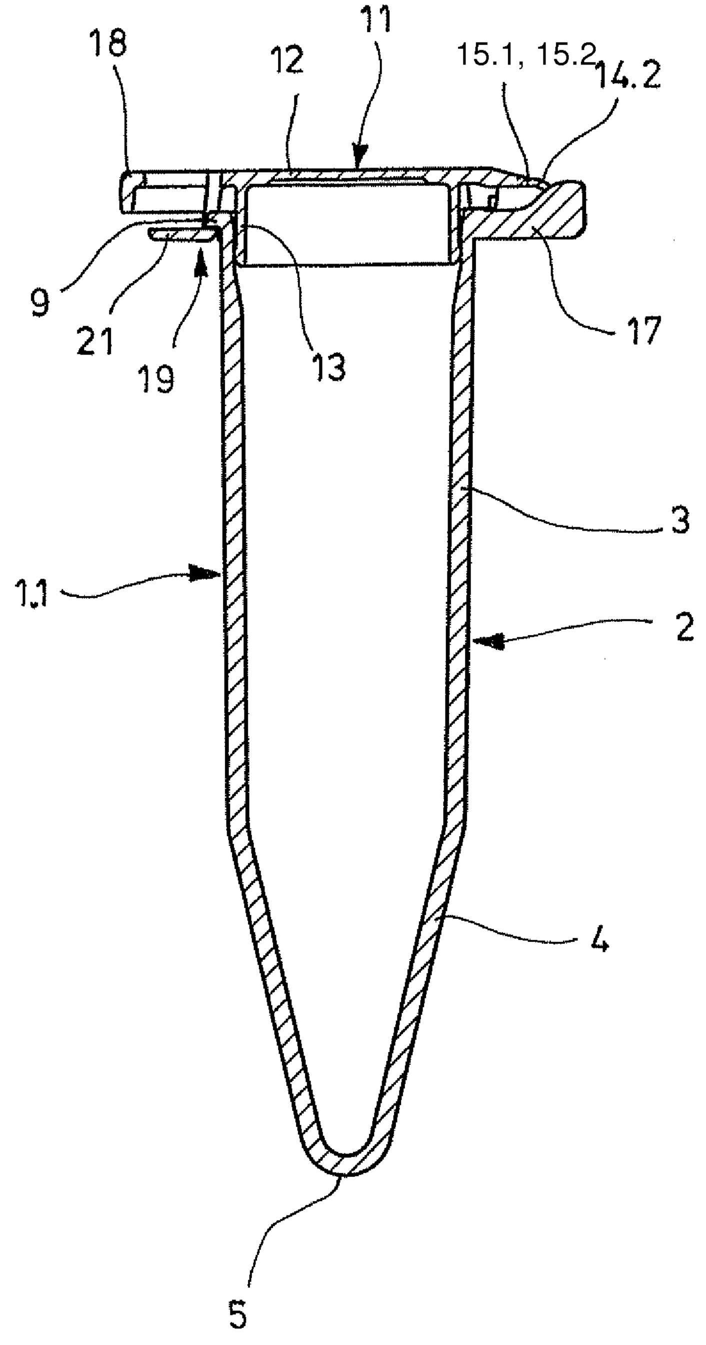
FIG. 2 shows said lidded container closed in a vertical section.
Figure 3B:
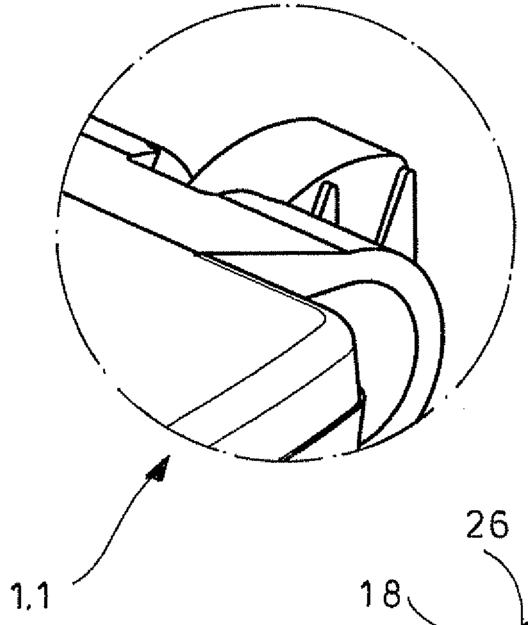
FIG. 3*a+b* show said lidded container in the closed state in a perspective view (FIG. 3*a*) and an enlarged detail b of FIG. 3*a* (FIG. 3*b*)
Figure 3A:
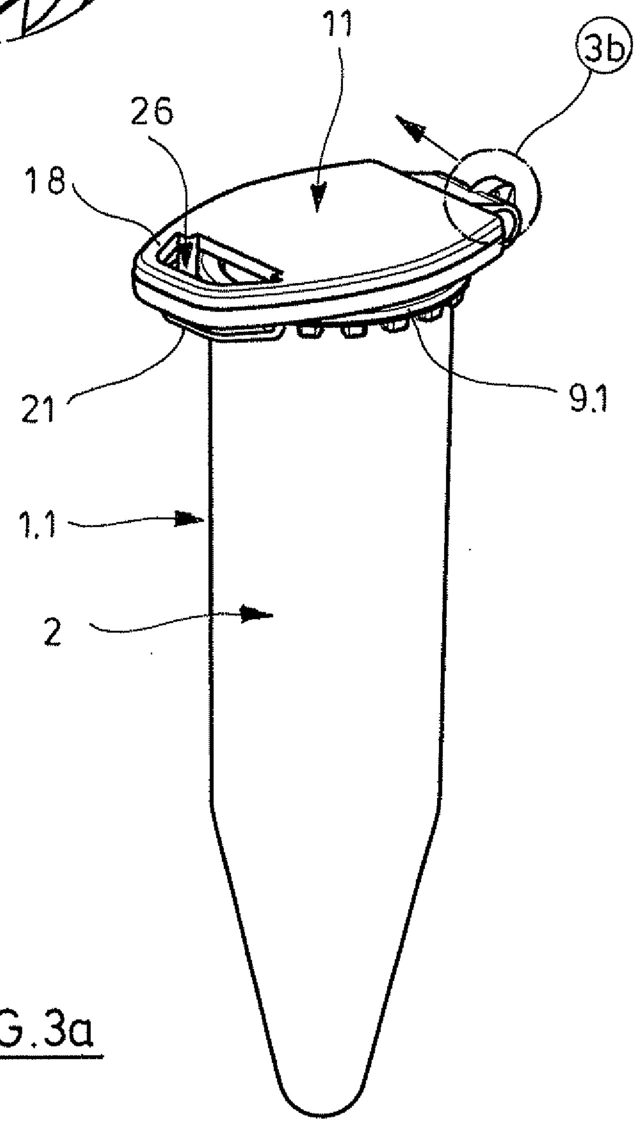

While this invention may be embodied in many different forms, there are described in detail herein a specific preferred embodiment of the invention. This description is an exemplification of the principles of the invention and is not intended to limit the invention to the particular embodiment illustrated In this application the terms "at the top" and "at the bottom" as well as "top side" and "bottom side" refer to the arrangement of the lidded container in the closed state with a vertically aligned tubular container, the container base being arranged at the bottom and the lid at the top.

The lidded container 1.1 in FIGS. 1 to 12 has a tubular container 2 with a circular cross section that possesses a hollow cylindrical section 3 at the top and a conical section 4 at the bottom. At the very bottom, the container 2 has a cup-shaped base 5. At the top, the container 2 has a container opening 6. Thereunder in the hollow cylindrical section 3, the container has an insertion region 7 tapering conically downwards and a circular cylindrical sealing region 8 thereunder.

At the upper margin, the container 2 has a peripheral flange 9.1, protruding radially outwardly in the form of a circular disc. A latching projection 9.2 is formed on the flange 9.1.

Below the flange 9.1 on the outer periphery of the container 2, a series of tine-like projections 10.1 are optionally arranged, and which serve for supporting on the edge of a container holder.

The lidded container 1.1 has a lid 11 which comprises a lid base 12 and a plug 13 protruding from below the lid base 12. The plug 13 has a hollow cylindrical plug section 13.1. At the lower end of the plug portion 13.1 the plug has a peripheral, outwardly protruding sealing bead 13.2.

The lid base 12 protrudes to all sides over the plug 13. The lid base 12 has an approximately elliptical contour 12.1. The extent of the lid base 12 in the direction of the main axis of the elliptical contour 12.1 is defined by two approximately straight lid edges 12.2, 12.3 which extend parallel to the auxiliary axis of the elliptical contour 12.1 (FIG. 6*b*).

Figure 8B:
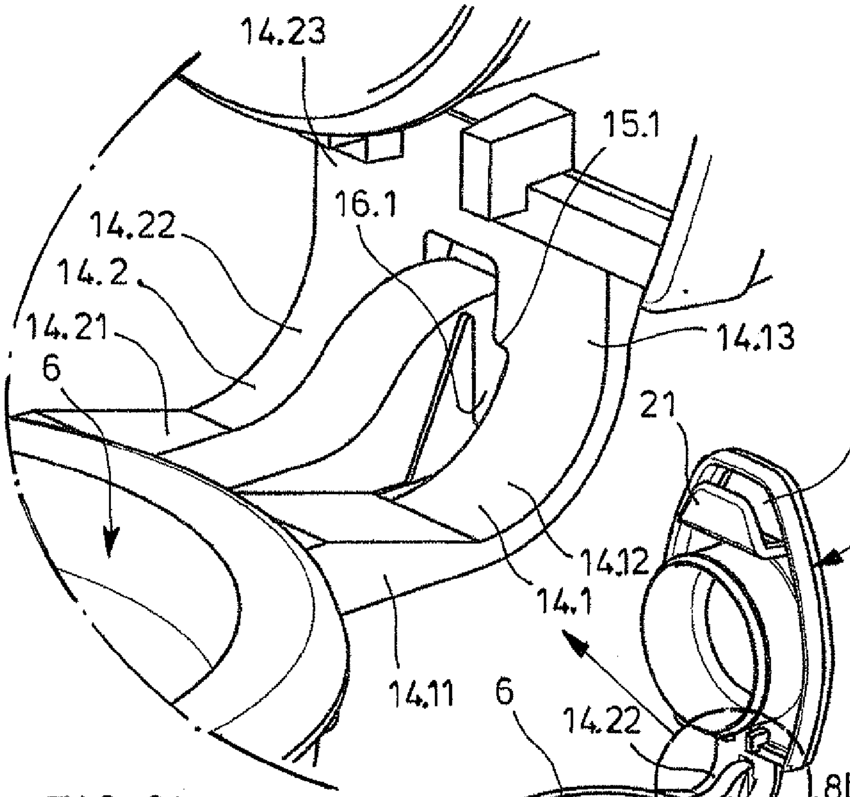
FIG. 8*a+b* show said lidded container with the lid locked in an intermediate position in a perspective view (FIG. 8*a*) and in an enlarged detail b of FIG. 8*a* (FIG. 8*b*)
Figure 8A:
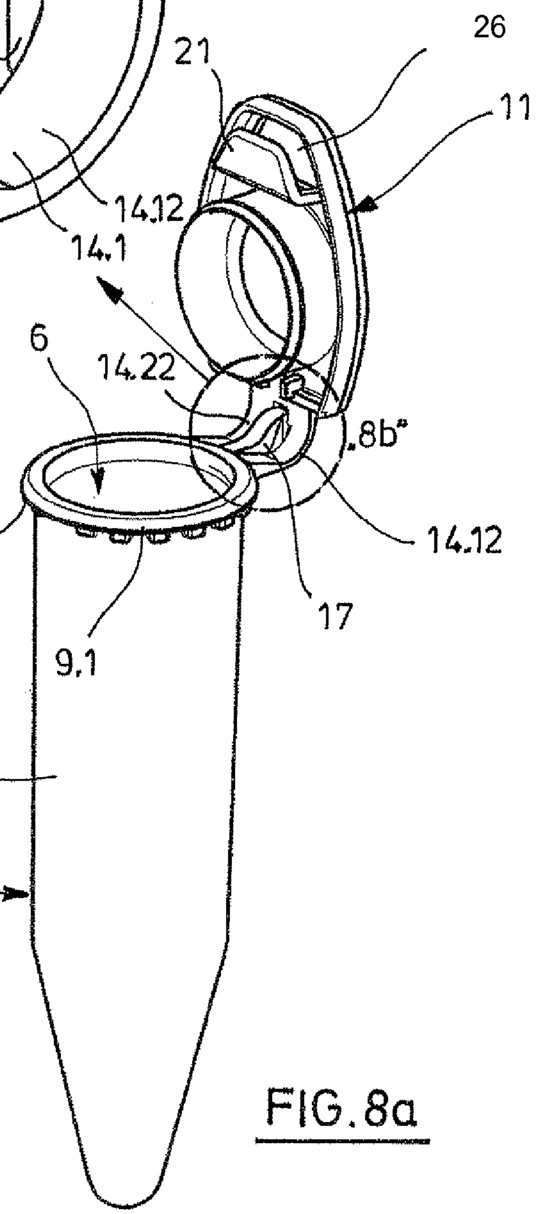
Figures 9A, 9B:
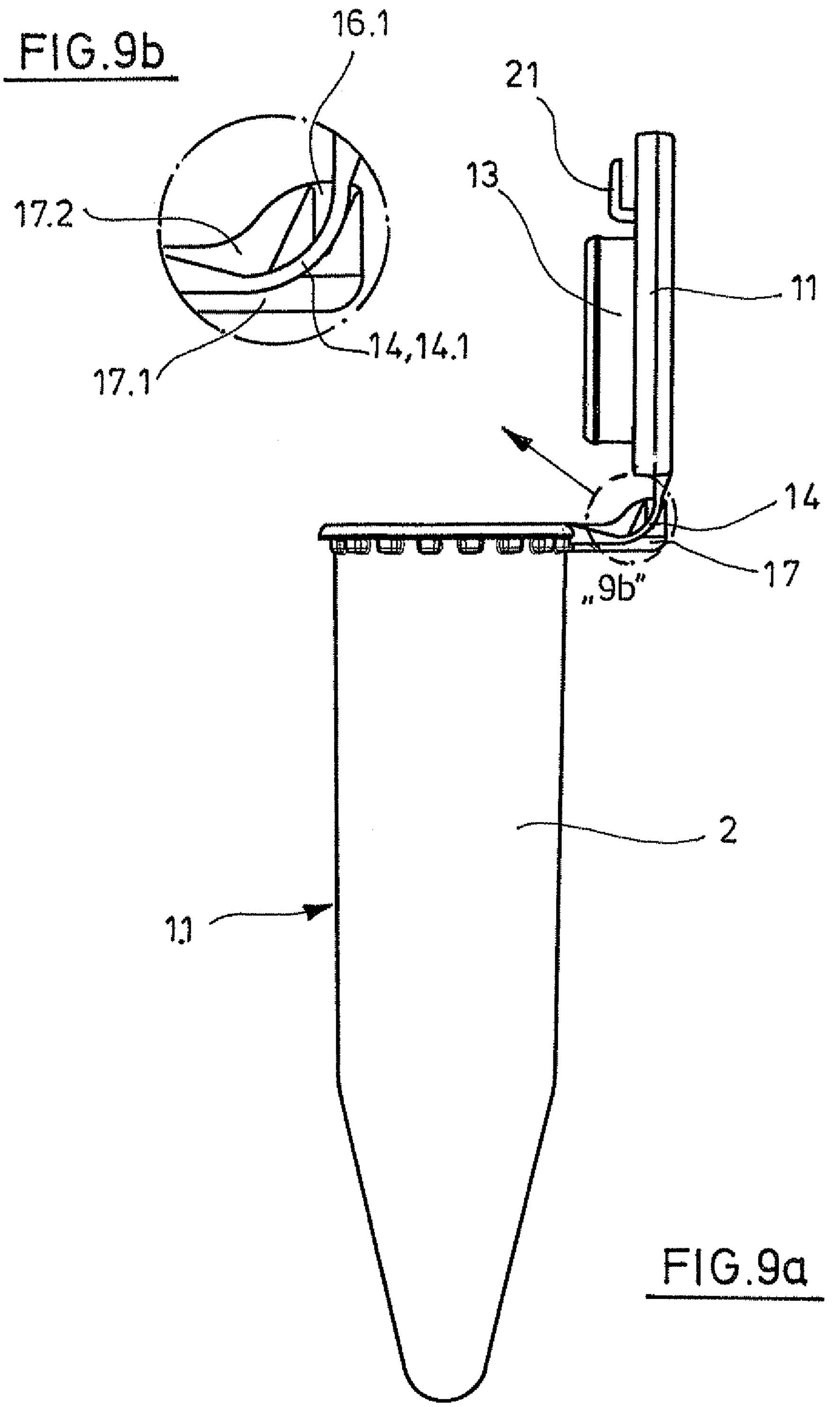
FIG. 9*a+b* show said lidded container with the lid locked in the intermediate position in side view (FIG. 9*a*) and in an enlarged detail b of FIG. 9*a* (FIG. 9*b*)

The outer margin of the lid base 12 is connected via a strap hinge 14 to the upper edge of the container 2. The strap hinge 14 is connected to the longer straight lid margin 12.2. The strap hinge 14 comprises two parallel hinge straps 14.1, 14.2 spaced apart from one another (FIG. 8). The hinge straps 14.1, 14.2 in each case have a more rigid first portion 14.11, 14.21 connected to the upper edge of the container 2 and adjacent thereto in each case a more flexible resilient portion 14.12, 14.22 and adjacent thereto a second more rigid portion 14.13, 14.23 connected to the outer edge of the lid base 12.

Preferably, the hinge straps 14.1, 14.2 are connected integrally to said container parts by injection-molding.

Figures 6A, 6B, 6C:
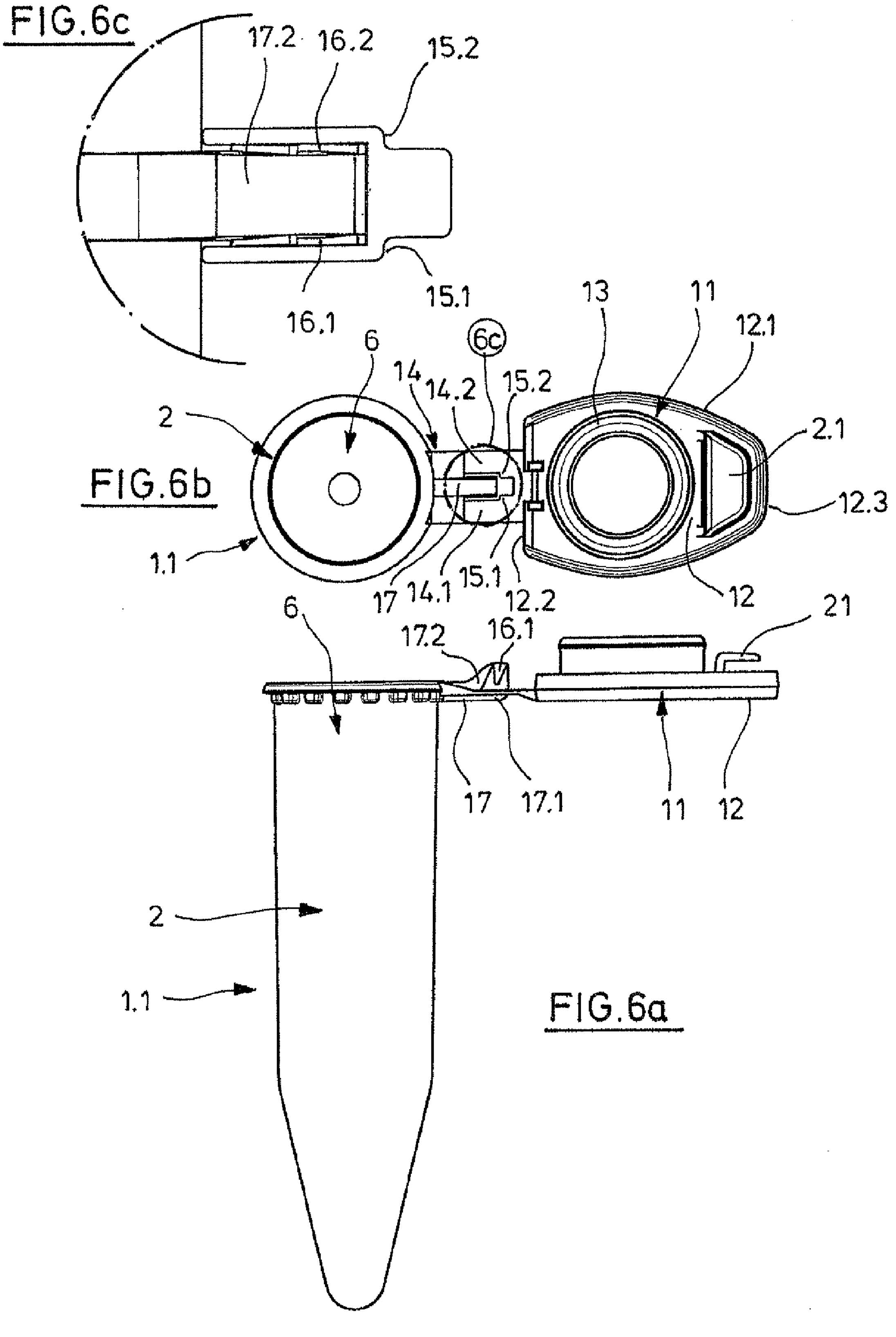
FIG. 6*a-c* shows said lidded container in the open state in a side view (FIG. 6*a*), in a plan view (FIG. 6*b*) and enlarged detail c of FIG. 6*b* (FIG. 6*c*)
Figure 7B:
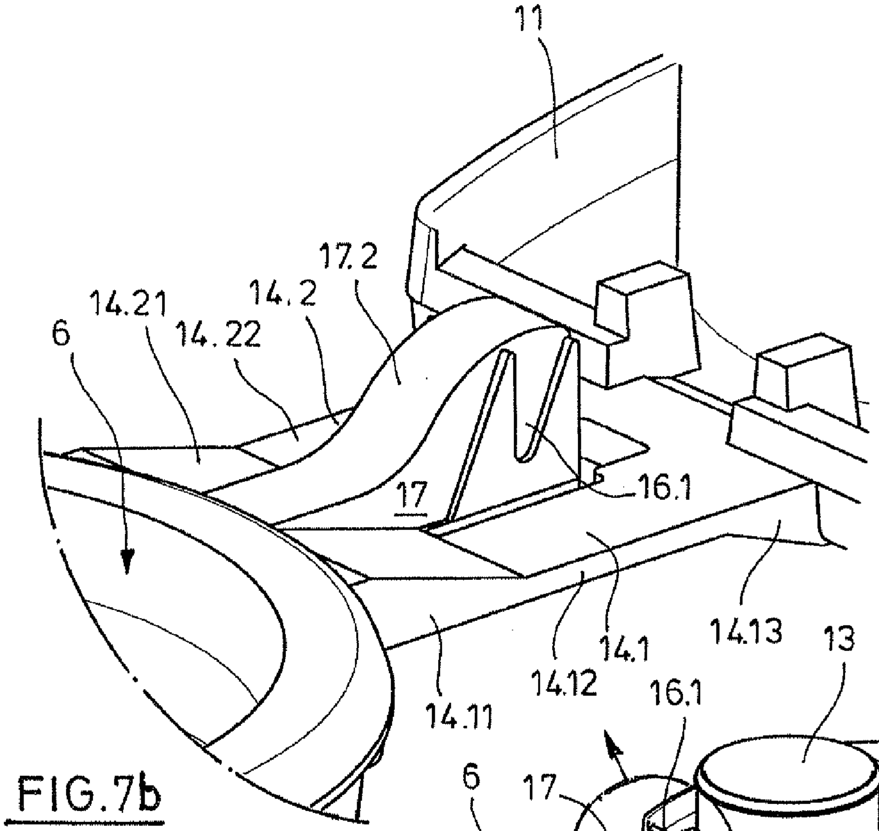
FIG. 7*a+b* show said lidded container in the open state in a perspective view (FIG. 7*a*) and an enlarged detail b of FIG. 7*a* (FIG. 7*b*)

The hinge straps 14.1, 14.2 have on the inside between the flexible portions 14.12, 14.22 and the second more rigid portions 14.13, 14.2.3 in each case a shoulder 15.1, 15.2 which form axial engagement means (FIG. 6*b, c*). Between the hinge straps 14.1, 14.2 V-shaped latching receivers 16.1, 16.2 are arranged on both sides of a support 17 protruding to the side of the container 2. The V-shaped latching receivers 16.1, 16.2 in each case are open at the top and to the side of the adjacent hinge straps 14.1, 14.2. They are defined by receiver edges 16.11, 16.12, 16.21, 16.22 oriented radially to the pivoting path of the lid 11 (FIG. 6*c*, 7*b*). The latching receivers constitute further axial engagement means.

The support 17 comprises the support part 17.1 which protrudes radially from the edge of the container. The support part 17.1 carries at the top a narrow, disc-shaped or rib-shaped support part 17.2. The disc-shaped support part 17.2 is provided on both flat outer faces with the latching receivers 16.1, 16.2 (FIG. 6).

Opposite the film hinge 14, the part of the lid base 12 protruding over the plug 13 to the side forms a lid projection 18. The lid projection 18 tapers towards the outer margin of the lid base 12. The lid projection 18 is delimited by the shorter straight lid edge 12.3. A latching device 19 is arranged below the lid projection 18.

The latching device 19 has a flexible connecting link 20 which, at the top, is connected to the bottom side of the lid projection 18. The connecting link 20 comprises two parallel connecting link strips 20.1, 20.2, which are spaced apart from one another. The connecting link strips 20.1, 20.2 are connected together at the lower end via a plate-shaped button 21 which protrudes outwardly to the side. A recess 22 is present in the connecting link strips 20.1, 20.2 above the button 21. The recess 22 is delimited at the bottom by the inner upper margin of the button 21. This margin forms a latching edge 23. The button 21 has a chamfer 24 below said latching edge on the inside and a radius 25 thereunder.

Figure 4:
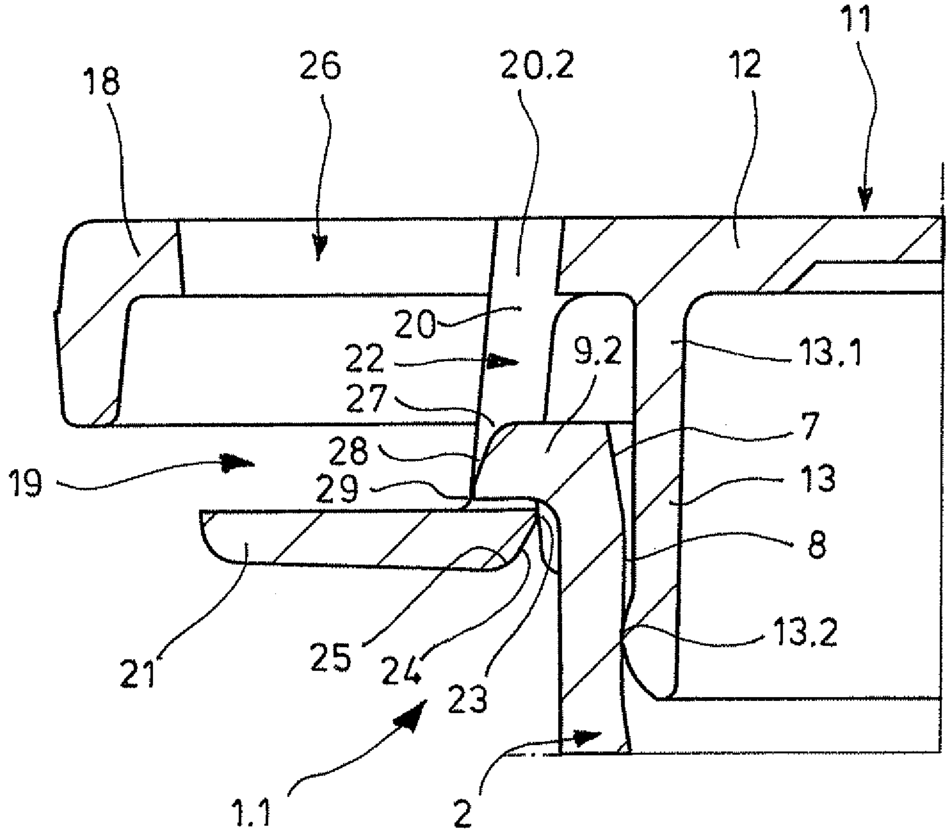
FIG. 4 shows the lid latch of said lidded container in the closed state in an enlarged vertical partial section.
Figure 5:
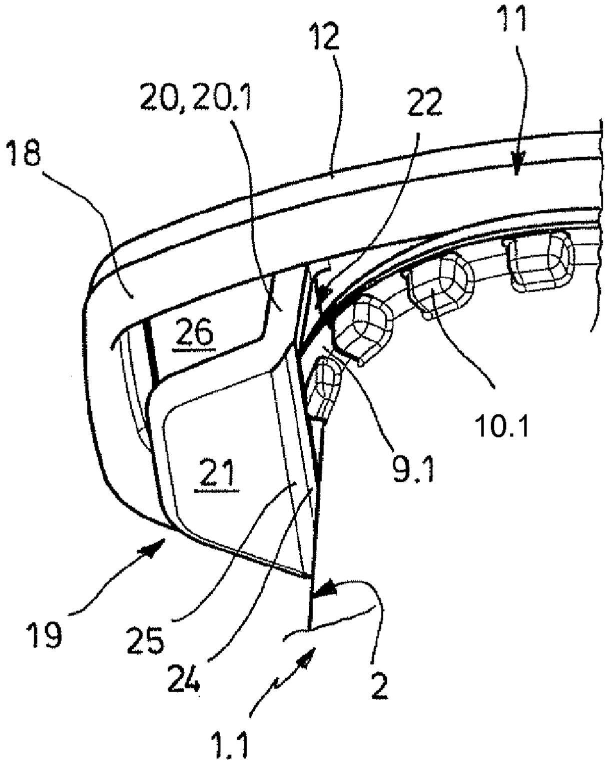
FIG. 5 shows said lid latch closed in a perspective partial view obliquely from below.

In the non-deflected state, which is shown in FIGS. 4 and 5, the button 21 is arranged below a congruent or respectively slightly larger lid recess 26 in the lid projection 18. As a result, an integral production of the entire lidded container 1.1 in one injection-molding process is possible by means of a single mold.

According to FIGS. 4 and 5, the lid 11 in the closed state is latched to the container 2. This is achieved by the latching edge 23 engaging below the flange 9.1 in a region free of pinnacle-like projections 10.1, which forms the latching projection 9.2. The latching projection 9.2 at the top has a radius 27 and thereunder a chamfer 28.

Figure 7A:
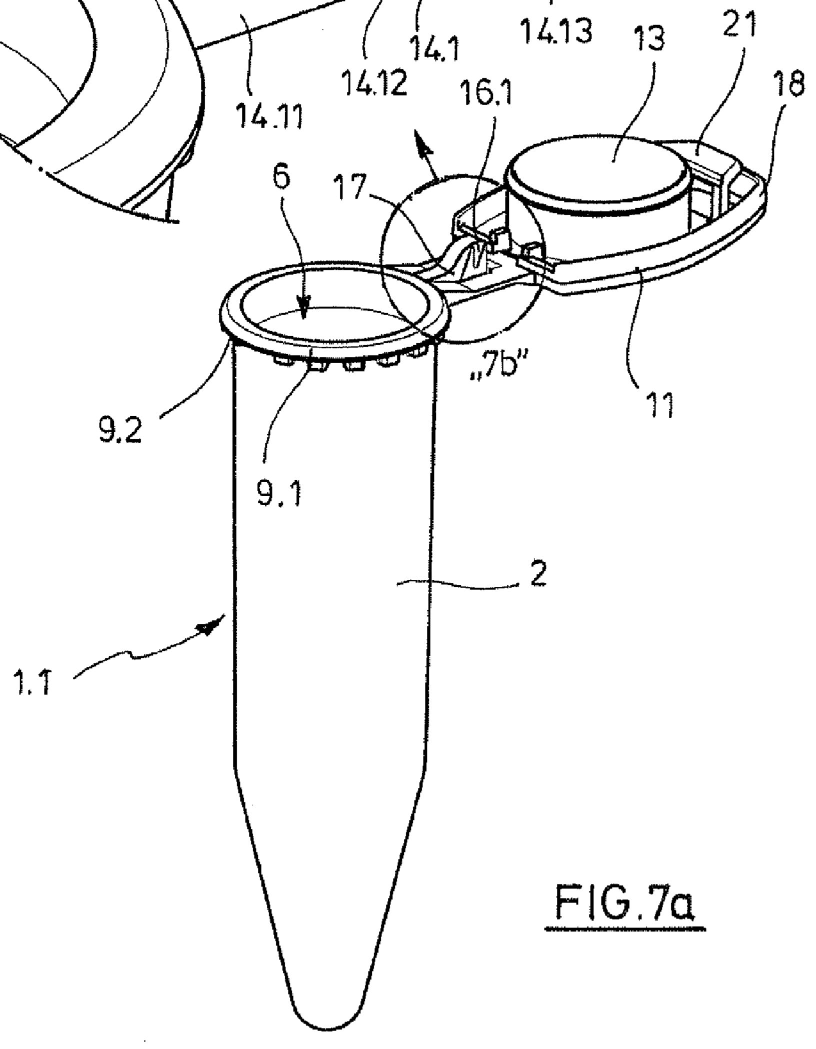

The lidded container 1.1 is produced in the open arrangement shown in FIGS. 6 and 7, by injection molding. Due to the shape which is free of undercuts, the lidded container 1.1 may be produced by means of a single injection-mold without a slide, the mold parts thereof having to be moved apart only along one axis for demolding.

The lid 11 may be closed by being pivoted to the closed position from the open position shown in FIGS. 6 and 7. To this end, the user presses against the outer face of the lid base 12. In an intermediate position according to FIGS. 8 and 9, the lid 11 is able to be locked by forcing the shoulders 15.1, 15.2 in the latching receivers 16.1, 16.2. In this case, the deviation of the shoulders 15.1, 15.2 outwardly to the side and to the rear is permitted by the flexibility of the shoulders 15.1, 15.2 and the strip regions 14.12, 14.22. As soon as the shoulders 15.1, 15.2 enter the region of the latching receivers 16.1, 16.2, due to the resilience of the shoulders 15.1, 15.2 and the strip regions 14.12, 14.22 they enter the latching receivers 16.1, 16.2. In this holding position, the shoulders engage behind the receiver edges 16.11, 16.21 and the lid 11 is held in this holding position by the resilience of the hinge straps 14.1, 14.2.

To close the lid fully, the user presses again against the outer face of the lid base 12. As a result, the lid 11 is pivoted to the closed position out of the holding position.

Thus the shoulders 15.1, 15.2 emerge from the openings of the latching receivers 16.1, 16.2, and do not collide with the receiver edges 16.12, 16.22. The receiver edges 16.12, 16.22 may alternatively be arranged so that they are located in the region where the shoulders 15.1, 15.2 pivot to the closed position and the latching receivers 16.1, 16.2 positively receive the shoulders 15.1, 15.2. To this end, the shoulders 15.1, 15.2 have to be forced out of the latching receivers 16.1, 16.2 by utilizing their flexibility, in order to pivot the lid 11 to the closed position.

Figure 10:
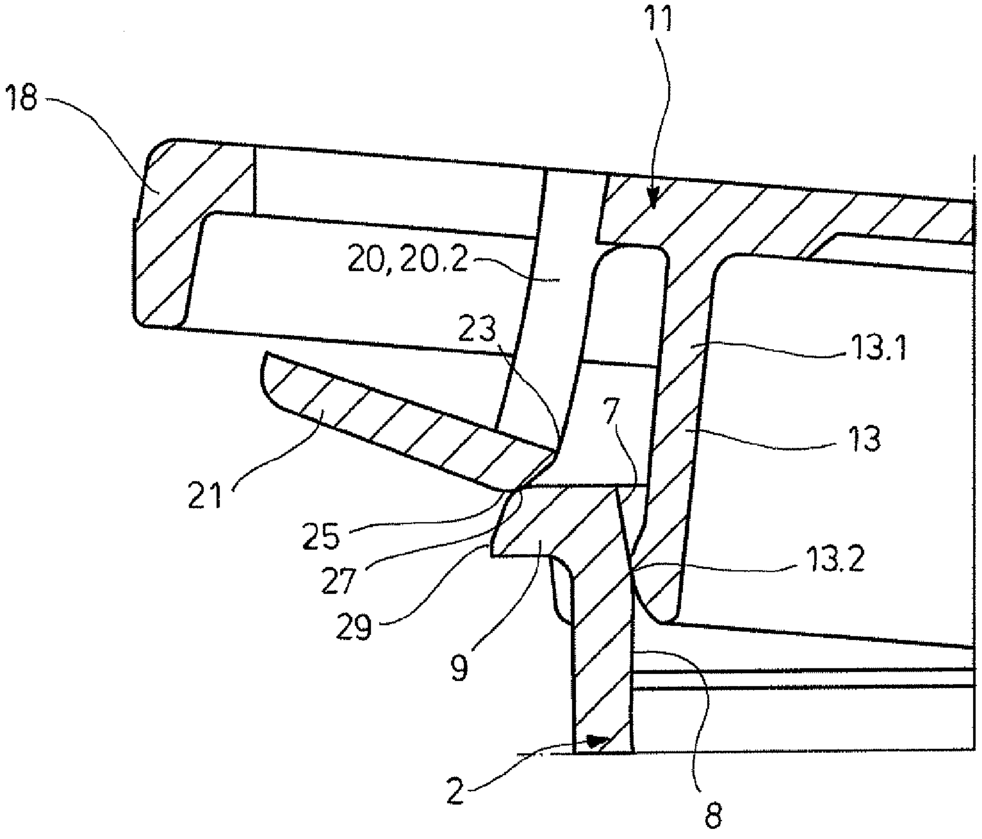
FIG. 10 shows said lid latch at the start of the latching process in an enlarged vertical partial section.

The lid 11 pivots with the plug 13 into the container opening 6, which is facilitated by the widened insertion region 7. Then the sealing bead 13.2 is inserted into the sealing region 8. Thus the button 21 with its radius 25 comes into contact with the radius 27 of the latching projection 9.2, as shown in FIG. 10. When pressing the lid 11 further shut, the connecting link 20 is deflected outwardly to the side. Due to the flexibility of the connecting link 20 and chamfers 24, 28 of the button 21 and latching projection 9.2, this requires slightly more force. When the latching edge 23 has reached the latching edge 29 of the latching projection 9.2 (see FIG. 11), the connecting link 20 springs towards the container 2, and the inner edge of the button 21 engages below the latching projection 9.2 (FIG. 4, 5). As a result, the latching is complete and the lid 11 secured on the container 2.

Figure 12:
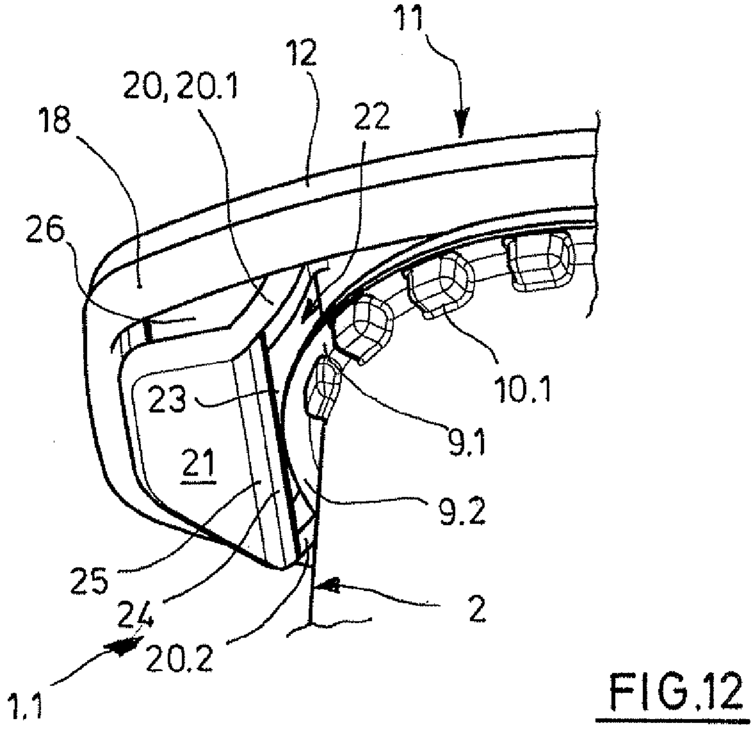
FIG. 12 shows said lid latch open in a perspective partial view obliquely from below.
Figure 11:
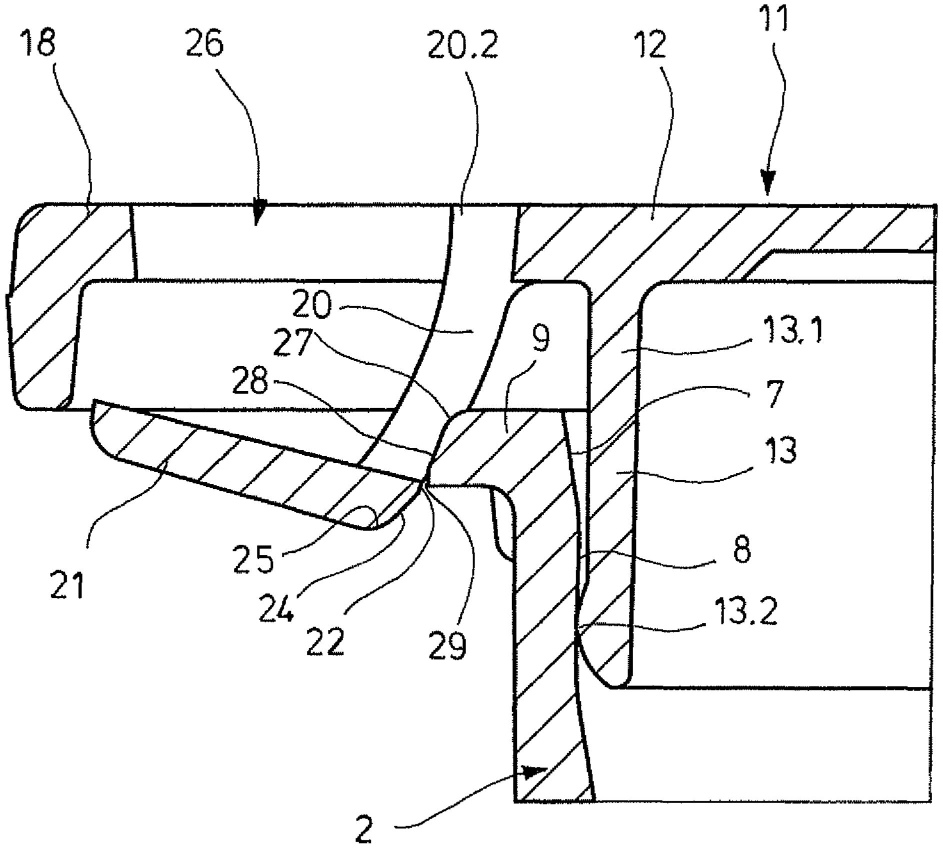
FIG. 11 shows said lid latch before completing the latching process in an enlarged vertical partial section.

To open the lid 11, the user presses from below against the button 21 so that said button is deflected to the side, as shown in FIGS. 11 and 12. By pressing against the button 21, the lid 11 is moved together with the plug 13 out of the container opening 6 and opened. In the open position, the lid 11 may be securely locked by the shoulders 15.1, 15.2 being engaged in the latching receivers 16.1, 16.2 (FIG. 8, 9).

Figure 13:
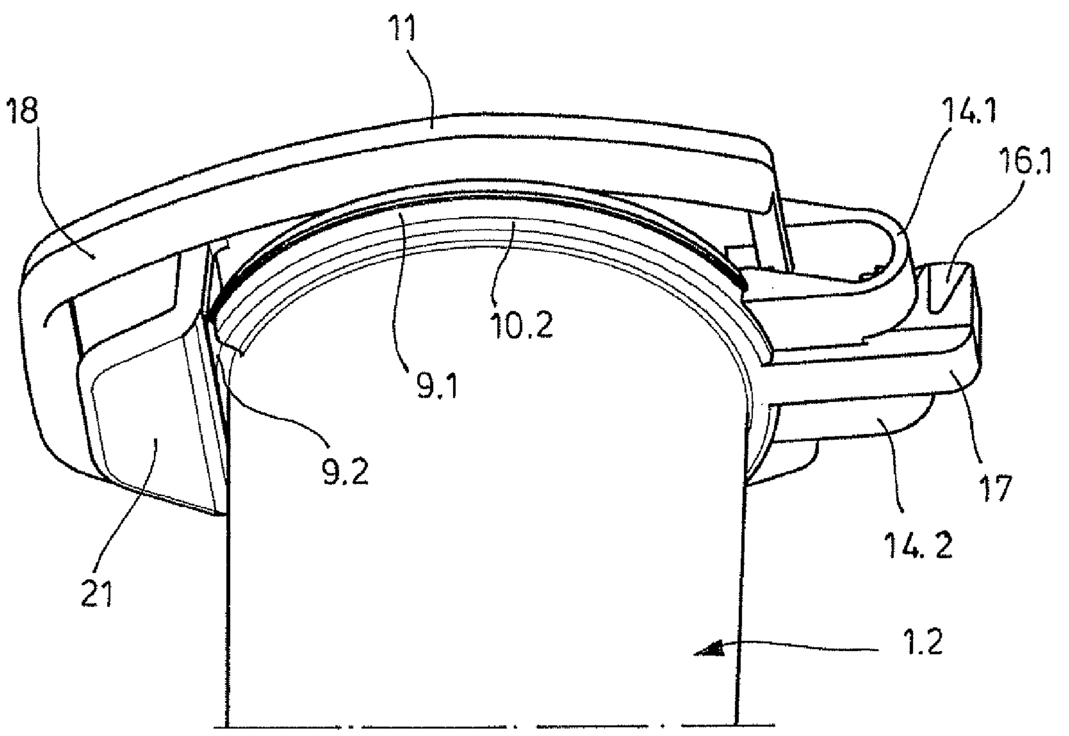
FIG. 13 shows an additional lidded container with a flange without pinnacle-like projections in a perspective partial view obliquely from below.

The lidded container 1.2 in FIG. 13 differs from that described above 1.1 in that the flange 9.1 at the bottom is not stabilized by pinnacle-like projections 10.1 but rather by a single, partially peripheral, bead-like projection 10.2 that is only interrupted in the area of the latching projection 9.2.

Figure 14:
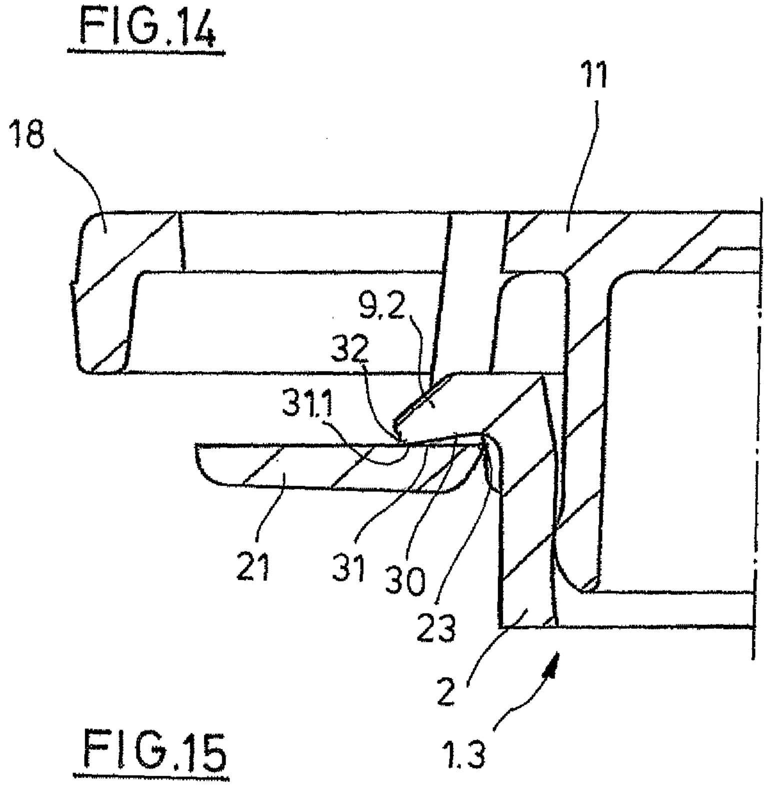
FIG. 14 shows an enlarged vertical partial vertical section of the lid latch of a modified lidded container having a chamfer on the bottom side of the latching projection when the pressure inside and outside of the container matches.

The latch according to FIG. 14 differs from the lid latch described above in that the latch projection 9.2 has a chamfer 30 on the bottom side. The chamfer 30 angles up-ward toward the container 2.

In a closed state, a contact area 31 on the top side of the button 2.1 with a section 31.1 at a distance from the latching edge 23 is assigned to, or respectively rests upon, the lowest area 32 of the latching projection 9.2. This is shown in FIG. 14. With reference to the container 2, the section 31.1 is arranged further to the outside than the connection of the connecting links 20.1, 20.2 to the lid base 12. It is sufficient when the section 31.1 is arranged further to the outside than the middle of the connection of the connecting links 20.1, 20.2 to the lid base 12 with reference to the container 2. FIG. 14 shows this in a situation in which the pressure inside the container corresponds to the ambient pressure.

Figure 15:
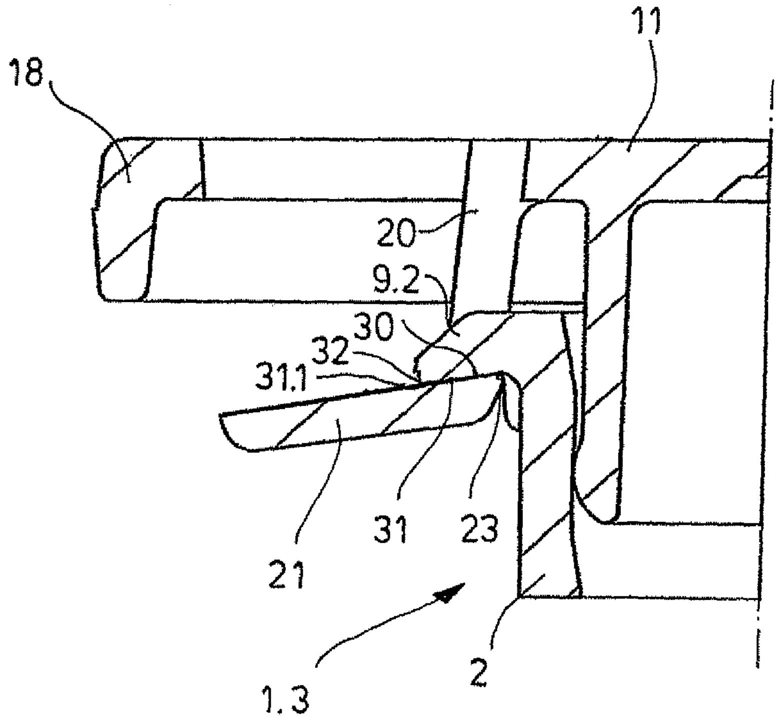
FIG. 15 shows an enlarged vertical partial section of the same lid latch when the inside container pressure is higher.

FIG. 15 shows the lidded container 1.3 in a situation in which the pressure inside the container 2 is higher than the ambient pressure. Due to the increased internal pressure or a force exerted from the outside on the lid base 12, the lid 11 is pressed upward. Since the section 31.1 is located further to the outside than the connection of the connecting links 20.1, 20.2, bending moment is exerted on the button 21 such that its contact area 31 lies flat against the chamfer 30. This prevents the button 21 from slipping off the latching projection 9.2 and additionally secures the lid 11 on the container 2. In this embodiment, increased pressure within the container or vertically acting force supports the latching of the lid 11 to the container 2.

Figure 16:
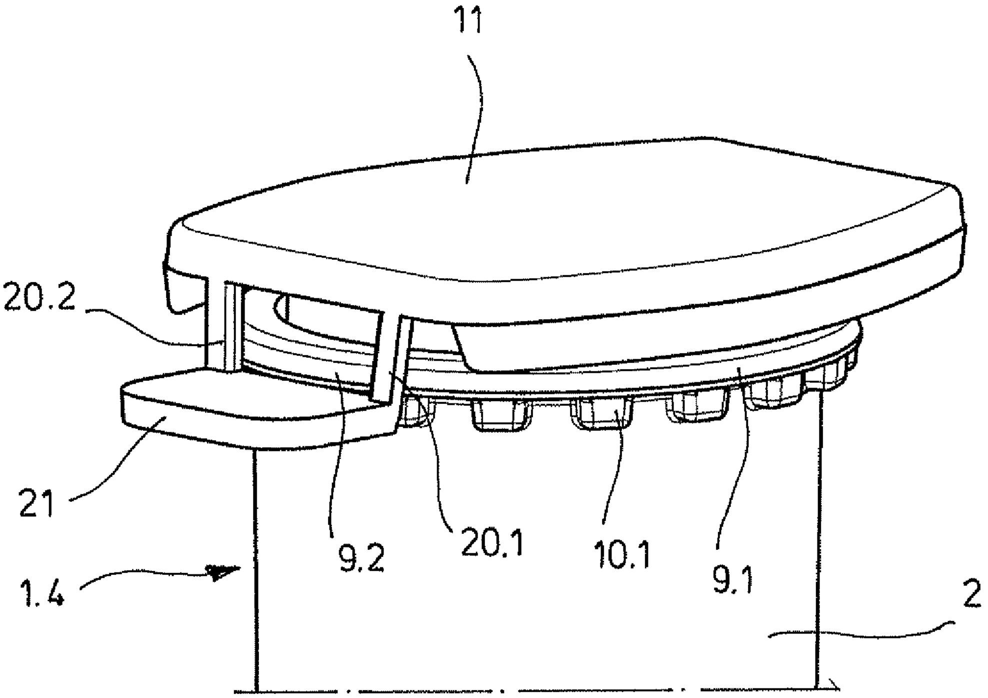
FIG. 16 shows a perspective partial view at an angle from above and from the side of a lidded container without a lid projection above the button in a locked state.
Figure 17:
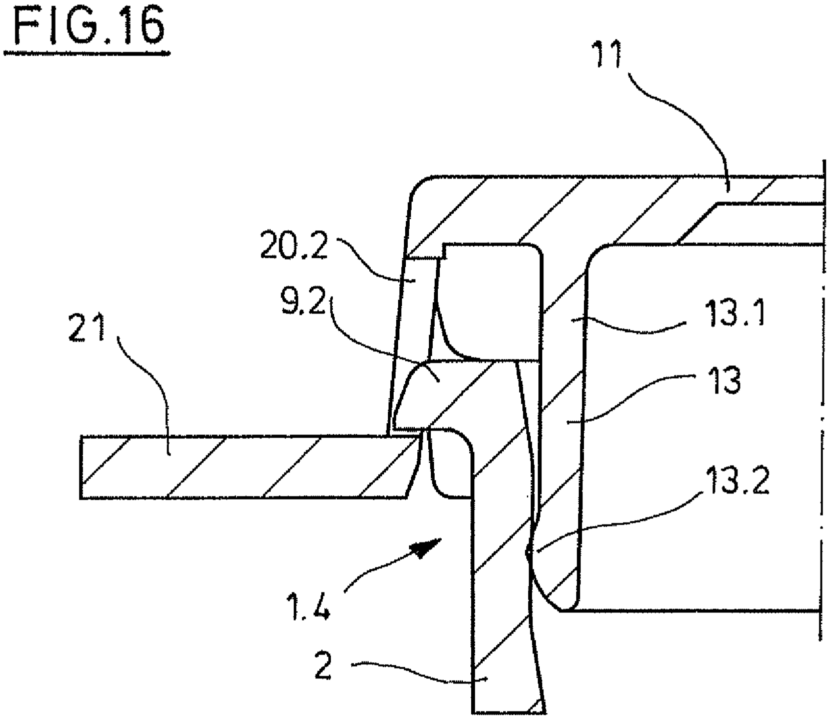
FIG. 17 shows the lid latch of said lidded container in an enlarged vertical partial section.
Figure 19:
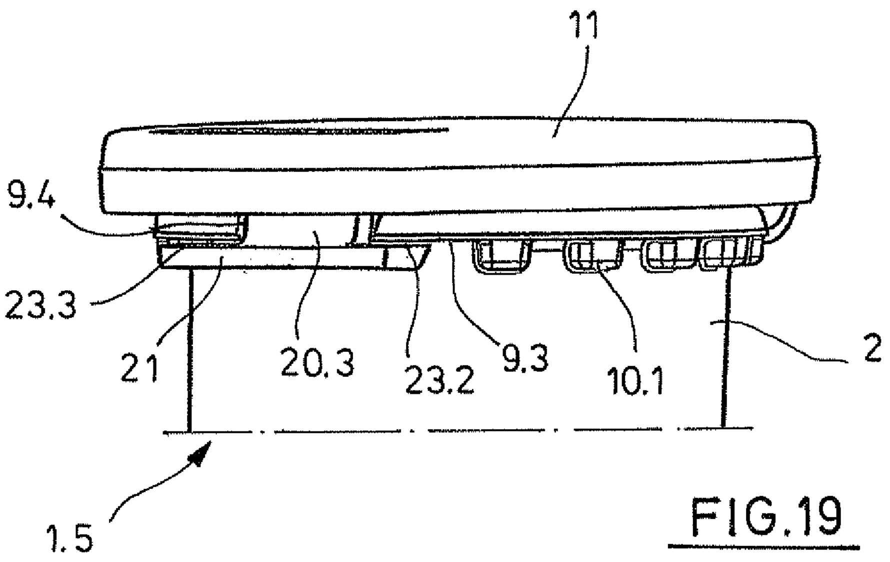
FIG. 19 shows said lidded container in an enlarged partial view from the same side.

The lidded container 1.4 in FIGS. 16 and 17 differs from lidded container 1.1 in FIG. 1-12 in that it does not have a lid projection 18. The advantage of this design is that manufacturing is more economical since the costs of materials and tools are saved.

Figure 18:
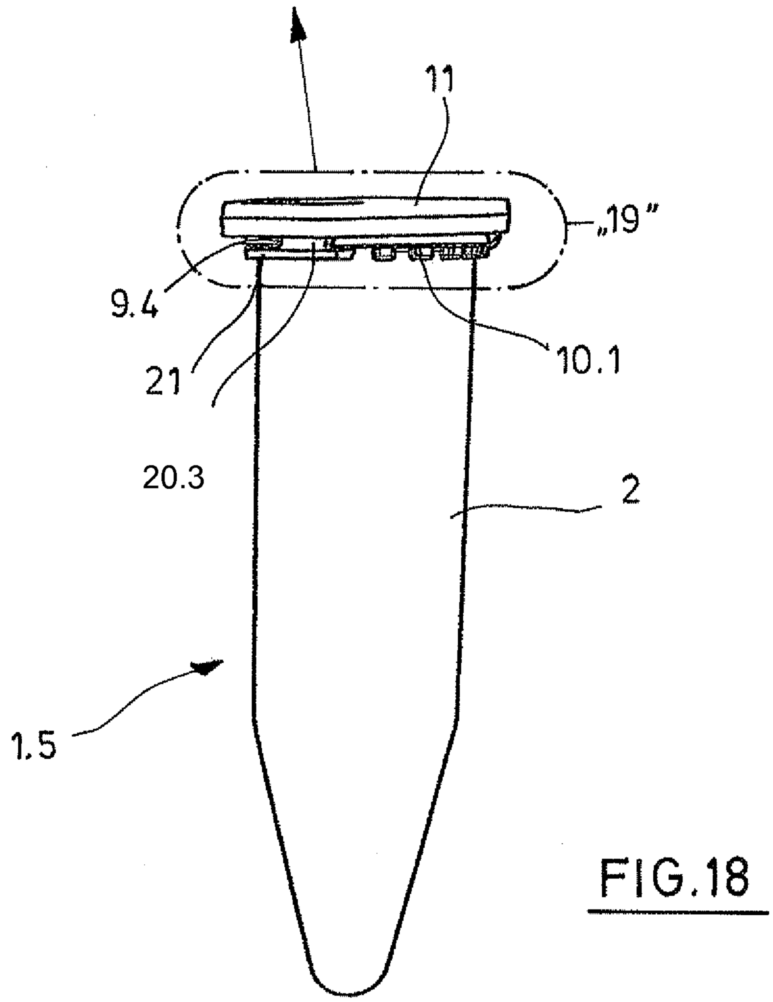
FIG. 18 shows a side view of a lidded container having a lid latch with a single connecting link strip and a button protruding at both sides.

In contrast to the lidded container 1.1 in FIGS. 1 to 12, the lidded container 1.5 in FIGS. 17 and 18 only has a single connecting link strip 20.3 that is connected at the bottom end with a plate-shaped button 21. The button 21 is wider than the connecting link strip 20.3 and projects from both sides of the connecting link strip 20.3. The inner, top margins of the button 21 form latching edges 23.2, 23.3. Thereunder, the button 21 has chamfers 24.2, 24.3 on the inside and radii 25.2, 25.3 underneath. The latching edges 22.2, 22.3 are locked at the bottom side of the latching projection 9.3. The latching projection 9.3 has a vertical cutout 9.4 assigned to the connecting link strips in which the connecting link strips 20.3 engage when the latching edges 23.2, 23.3 engage under the latching projection 9.3.

The lidded container 1.6 according to FIGS. 20 and 21 has three lid latches 9.2, 19 evenly distributed over the perimeter. These are designed corresponding to the lid latch 9.2, 19 of the lidded container 1.1 in FIGS. 1 to 12. A hinge is between the lid 11 and container 2.

The lid 11 can be evenly latched to the container 2 by means of the three lid latches 9.2, 19. This provides security against unintentionally opening the container and increases the seal. This is particularly true for lidded containers having a comparatively large diameter (for example with a volume of 10 mL and more).

The lid 11 is closed by pressing it downwards on the container 2 in a vertical direction until all latches are latched. To open, all of the buttons 21 can be actuated simultaneously, or first two buttons 21 and then another button 21, or the buttons can be sequentially actuated to gradually release the lid 11 from the latching projections 9.2 on the flange 9.1 of the container 2.

Figure 23:
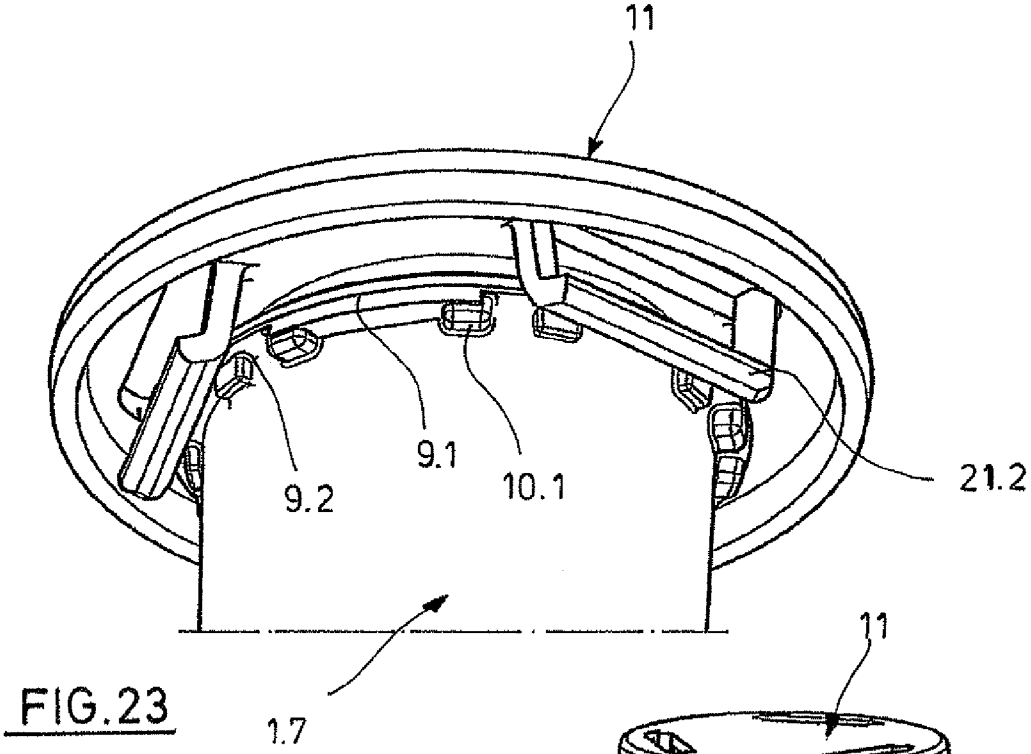
FIG. 23 shows said lidded container in a closed state in an enlarged perspective partial view at an angle from below and from the side.
Figure 22:
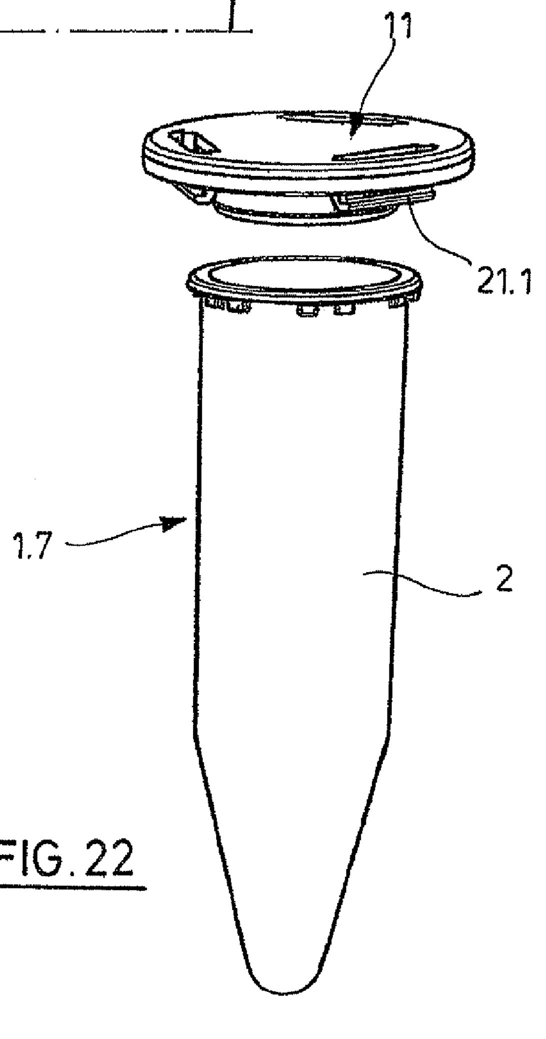
FIG. 22 shows another lidded container having a plurality of latches with strongly reduced buttons and without hinge with an open lid in a perspective view at an angle from above and from the side.

FIGS. 22 and 23 show a lidded container 1.7 with less pronounced buttons 21.2 than in the aforementioned design. The buttons 21.2 may be actuated with a thumb, if applicable. With this lidded container 1.7, it is also possible to release the lid 11 from the container 2 by pressing upward.

This completes the description of the preferred and alternate embodiments of the invention. Those skilled in the art may recognize other equivalents to the specific embodiment described herein which equivalents are intended to be encompassed by the claims attached hereto.

What is claimed is:

1. A lidded container made of plastic for laboratory use having a tubular container (2) which at the bottom has a container base (5), at the top a container opening (6) and below the container opening (6) a sealing region (8) on the internal wall, a lid (11) which has a lid base (12) and a plug (13) protruding from the inside of the lid base, and which may be inserted through the container opening (6) into a sealed position in the sealing region (8), and locking means for releasably locking the lid (11) to the container (2) comprising at least one latching projection projecting radially outward at the top edge of the container (9.2), and at least one flexible and elastic connecting link (20) projecting from the bottom side of the lid base (12) on which a latching edge (23) is arranged at a distance from the lid base vertically below the connection of the connecting link (20) to the lid base, and the latching edge can be snapped into the sealing area (8) below the latching projection (9.2) when the plug (13) is introduced, wherein the latching edge (23) of the bottom margin is a cutout (22) in the connecting link (20).

2. The lidded container according to claim 1, wherein the latching projection (9.2) is formed on a flange (9.1) that at least partially surrounds the perimeter of the top margin of the container (2).

3. The lidded container according to claim 1, in which the latching projection (9.2) on the outside and/or the connecting link (20) on the inside has an outer and/or inner chamfer (28, 24) neighboring the latching edge so that the connecting link (20) is increasingly deflected to the side when the plug (13) is inserted into the container (2).

4. The lidded container according to claim 1, in which the latching projection (9.2) at the top and/or the connecting link (20) at the bottom has a radius (27, 25).

5. The lidded container according to claim 1, in which the lid base (12) has a lid projection (18) projecting laterally to the outside that extends radially beyond the latching projection (9.2) when the plug (13) is inserted into the sealing region (8) to seal.

6. The lidded container according to claim 5, in which the lid projection (18) extends outward radially at least as far as a button (21) projecting outward to the side from the connecting link (20) when the plug (13) is inserted into the sealing region (8) to seal.

7. The lidded container according to claim 5, in which the button (21) is arranged in the direction of insertion of the plug (13) below a congruent lid cutout (26) in the lid projection (18).

8. The lidded container according to claim 5, in which the width of the lid projection (18) decreases toward the outer end of the lid connecting link (18).

9. The lidded container according to claim 1, in which a hinge (14) is arranged between the lid (12) and container (2).

10. The lidded container according to claim 9, in which the hinge (14) is a strap hinge by means of which the container (2) is integrally connected to the lid (11).

11. The lidded container according to claim 9, which has a device for locking (15, 16) the lid (11) in an open position next to the hinge (14).

12. The lidded container according to claim 1, in which the connecting link (20) has two lateral connecting link strips (20.1, 20.2) that are connected at the top to the lid base (12) and at the bottom to a button (21), and the cutout (22) is between them, wherein an inner, top margin of the button (21) forms the latching edge.

13. The lidded container according to claim 1, in which the container (2), adjacent to the container opening (6), has an insertion region (7) widening towards the upper edge of the container (2) for the plug (13) and the sealing region (8) thereunder.

14. The lidded container according to claim 1, in which the plug (13) is a hollow cylinder.

15. The lidded container according to claim 1, in which the plug (13) has a peripheral sealing bead (13.2) on the external periphery.

16. The lidded container according to claim 1 which is produced from a polyolefin.

17. The lidded container according to claim 1 which is injection-molded from plastic.

18. A lidded container made of plastic for laboratory use having a tubular container (2) which at the bottom has a container base (5), at the top a container opening (6) and below the container opening (6) a sealing region (8) on the internal wall, a lid (11) which has a lid base (12) and a plug (13) protruding from the inside of the lid base, and which may be inserted through the container opening (6) into a sealing position in the sealing region (8), and locking means for releasably locking the lid (11) to the container (2) comprising at least one latching projection (9.2) projecting radially outward at the top edge of the container, at least one flexible and elastic connecting link (20) projecting from the bottom side of the lid base (12) on which a latching edge (23) is arranged at a distance from the lid base (12) vertically below the connection of the connecting link (20) to the lid base (12), and the latching edge can be snapped into the sealing area (8) below the latching projection (9.2) when the plug (13) is introduced, and a button (21) projecting outward to the side from the connecting link (20), and the latching of the latching edge (23) to the latching projection (9.2) can be released by pressing against the button (21) from below, wherein an outward pivoting motion of the connecting link is controlled when the button is pushed.

19. The lidded container made of plastic for laboratory use comprising a tubular container (2) which at the bottom has a container base (5), at the top a container opening (6) and below the container opening (6) a sealing region (8) on the internal wall, a lid (11) which has a lid base (12) and a plug (13) protruding from the inside of the lid base, and which may be inserted through the container opening (6) into a sealing position in the sealing region (8), and locking means for releasably locking the lid (11) to the container (2) comprising at least one latching projection (9.2) projecting radially outward on the top edge of the container having a chamfer (30) on the bottom side angled upward toward the container, at least one flexible and elastic connecting link (20) projecting from the bottom side of the lid base (12) on which a contact area (31) with a latching edge (23) is arranged on the side facing the container at a distance from the lid base (12) and can snap under the latching projection (9.2) when the plug (13) is introduced into the sealing region (8) so that the contact area (31) is located below the lowest area (32) of the latching projection (9.2) with a section (31.1) located further to the outside than the connection of the connecting link (20) to the lid base (12), and the contact area (31) lies against the chamfer (30) when force is exerted vertically on the bottom side of the lid base (12).

20. The lidded container made of plastic for laboratory use having a tubular container (2) which at the bottom has a container base (5), at the top a container opening (6) and below the container opening (6) a sealing region (8) on the internal wall, a lid (11) which has a lid base (12) and a plug (13) protruding from the inside of the lid base, and which may be inserted through the container opening (6) into a sealed position in the sealing region (8), and locking means for releasably locking the lid (11) to the container (2) comprising at least one latching projection projecting radially outward at the top edge of the container (9.2), and a plurality of spaced, flexible and elastic connecting links (20) projecting from the bottom side of the lid base (12) on each of which a latching edge (23) is arranged at a distance from the lid base (12) that can be snapped into the sealing region (8) below the latching projection (9.2) when the plug (13) is introduced.

21. A lidded container made of plastic for laboratory use having a tubular container (2) which at the bottom has a container base (5), at the top a container opening (6) and below the container opening (6) a sealing region (8) on the internal wall, a lid (11) which has a lid base (12) and a plug (13) protruding from the inside of the lid base, and which may be inserted through the container opening (6) into a sealing position in the sealing region (8), and locking means for releasably locking the lid (11) to the container (2) comprising at least one latching projection (9.2) projecting radially outward at the top edge of the container, at least one flexible and elastic connecting link (20) projecting from the bottom side of the lid base (12) on which a latching edge (23) is arranged at a distance from the lid base (12) vertically below the connection of the connecting link (20) to the lid base (12), and the latching edge can be snapped into the sealing area (8) below the latching projection (9.2) when the plug (13) is introduced, and a button (21) projecting outward to the side from the connecting link (20), and the latching of the latching edge (23) to the latching projection (9.2) can be released by pressing against the button (21) from below, wherein an outward pivoting motion of the connecting link is controlled when the button is pushed, in which the connecting link (20) has a single connecting link strip (20.3) that is connected at the top to the lid base (12) and at the bottom to the button (21) which is wider than the connecting link strip (20.3), and at least one inner, top margin of the button (21) projecting laterally from the connecting link strip (20.3) forms the latching edge (23.2, 23.3).

22. A lidded container made of plastic for laboratory use having a tubular container (2) which at the bottom has a container base (5), at the top a container opening (6) and below the container opening (6) a sealing region (8) on the internal wall, a lid (11) which has a lid base (12) and a plug (13) protruding from the inside of the lid base, and which may be inserted through the container opening (6) into a sealed position in the sealing region (8), and locking means for releasably locking the lid (11) to the container (2) comprising at least one latching projection projecting radially outward at the top edge of the container (9.2), and at least one flexible and elastic connecting link (20) projecting from the bottom side of the lid base (12) on which a latching edge (23) is arranged at a distance from the lid base (18) vertically below the connection of the connecting link (20) to the lid base (18), and the latching edge can be snapped into the sealing area (8) below the latching projection (9.2) when the plug (13) is introduced, and a button (21) projecting outward to the side from the connecting link (20), and the latching of the latching edge (23) to the latching projection (9.2) can be released by pressing against the button (21) from below, wherein the connecting link (20) has two lateral connecting link strips (20.1, 20.2) that are connected at the top to the lid base (12) and at the bottom to the button (21), and the cutout (22) is between them, wherein the inner, top margin of the button (21) forms the latching edge (23.1).

* * * * *